United States Patent
Sudhakar et al.

(10) Patent No.: US 11,197,823 B2
(45) Date of Patent: *Dec. 14, 2021

(54) TOPIRAMATE ORAL LIQUID SUSPENSION AND USE THEREOF

(71) Applicant: OWP Pharmaceuticals, Inc., Naperville, IL (US)

(72) Inventors: Paul Sudhakar, Shawnee, KS (US); Scott Boyer, West Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/951,869

(22) Filed: Nov. 18, 2020

(65) Prior Publication Data

US 2021/0069107 A1 Mar. 11, 2021

Related U.S. Application Data

(63) Continuation-in-part of application No. 16/946,132, filed on Jun. 8, 2020.

(60) Provisional application No. 62/858,415, filed on Jun. 7, 2019.

(51) Int. Cl.

| | |
|---|---|
| *A61K 9/00* | (2006.01) |
| *A61K 31/7048* | (2006.01) |
| *A61K 47/10* | (2017.01) |
| *A61K 47/14* | (2017.01) |
| *A61K 47/36* | (2006.01) |
| *A61K 47/38* | (2006.01) |
| *A61K 47/02* | (2006.01) |
| *A61K 9/10* | (2006.01) |
| *A61K 47/12* | (2006.01) |

(52) U.S. Cl.
CPC .......... *A61K 9/0095* (2013.01); *A61K 9/0056* (2013.01); *A61K 9/10* (2013.01); *A61K 31/7048* (2013.01); *A61K 47/02* (2013.01); *A61K 47/10* (2013.01); *A61K 47/12* (2013.01); *A61K 47/14* (2013.01); *A61K 47/36* (2013.01); *A61K 47/38* (2013.01)

(58) Field of Classification Search
CPC .......... A61K 47/26; A61K 47/12; A61K 9/08; A61K 47/10; A61K 47/38; A61K 47/36; A61K 47/20; A61K 31/36; A61K 47/14; A61K 47/02; A61K 9/0053
See application file for complete search history.

(56) References Cited

PUBLICATIONS

NAMI: National Alliance on Mental Illness, Mental Health Conditions, pp. 1-6, Retrieved Feb. 8, 2021 (Year: 2021).*
Kaufman, Antiepileptic Drugs in THe Treatment of Pychiatric Disorders, Epilepsy & Behavior, 21, pp. 1-11. (Year: 2011).*
MedlinePlus Drug Information, Topiramate, pp. 1-8, retrieved Feb. 8, 2021. (Year: 2021).*
"Handbook of Pharmaceutical Excipients," Rowe et al., Eds., 8th Edition, Pharmaceutical Press (2017).
Non-Final Office Action, U.S. Appl. No. 16/946,132, filed Feb. 17, 2021, 11 pgs.
Notice of Allowability, U.S. Appl. No. 16/946,132, filed Jul. 23, 2021, 5 pgs.
Notice of Allowance and Fee(s) Due, U.S. Appl. No. 16/946,132, filed Jul. 8, 2021, 8 pgs.

* cited by examiner

*Primary Examiner* — Lezah Roberts
(74) *Attorney, Agent, or Firm* — Gary J. Speier; Carlson, Caspers, Vandenburgh & Lindquist, P.A.

(57) ABSTRACT

Provided herein is an oral liquid suspension that includes topiramate, as well as methods of medical treatment that include orally administering the oral liquid suspension.

23 Claims, No Drawings

TOPIRAMATE ORAL LIQUID SUSPENSION AND USE THEREOF

RELATED U.S. APPLICATION DATA

This application is a continuation-in-part (CIP) of patent application Ser. No. 16/946,132 filed Jun. 8, 2020 which application claims priority to provisional patent application No. 62/858,415 filed on Jun. 7, 2019; the contents of which are incorporated by reference herein in its entirety.

BACKGROUND OF THE INVENTION

Epilepsy is a disease of the nervous system which is caused by brain dysfunction due to excessive discharge of the nerve cells in the brain. It is estimated that the incidence rate of epilepsy is from about 0.3% to 0.5% globally. The morbidity rate is from about 5 to 10 people per 1000 people. Epilepsy is a serious threat to people's health and affects their daily lives.

Topiramate is an antiepileptic drug and its chemical structure relates to amino-sulfamate monosaccharide. Topiramate was first developed by Johnson & Johnson Company, Inc. USA. It was marketed under the brand name of Topamax in the UK in 1995. Based on in-vitro studies of neurons in electrophysiological and biochemical experiments, it was found that there were three mechanisms of antiepileptic action. Firstly, topiramate blocks the neuron's depolarization, which indicates that it can block sodium channels. Secondly, topiramate can increase the frequency of activation of γ-aminobutyrate (GABA) receptors by GABA and enhance the ability of influx of chloride ions which indicates that topiramate can enhance the role of inhibitory central neurotransmitters. Thirdly, topiramate can reduce the activity of glutamate AMPA receptors which indicates that topiramate can reduce the effect of excitatory central neurotransmitters.

Topiramate is a white crystalline powder with a bitter taste. It is freely soluble in acetone, dimethyl sulfoxide, ethanol, and alkaline solutions containing sodium hydroxide or sodium phosphate. Its solubility in water is approximately 9.8 mg/mL at room temperature.

Thus, to obtain a topiramate formulation with stable chemical properties and/or desired sustained release effect is highly desirable.

SUMMARY OF THE INVENTION

The present invention provides for an oral liquid suspension that includes: topiramate, preservative, sweetener, solvent, anticaking agent, viscosifying agent, suspending agent, pH adjuster, and taste-masking agent.

The present invention also provides for an oral liquid suspension that includes: topiramate, preservative, sweetener, solvent, anticaking agent, viscosifying agent, suspending agent, flavoring agent, colorant, pH adjuster, and taste-masking agent.

The present invention also provides for an oral liquid suspension that includes: 2,3:4,5-Di-O-isopropylidene-β-D-fructopyranose sulfamate (topiramate); water; glycerin; propylene glycol; polyethylene glycol; methylparaben; sodium benzoate; sorbitol; saccharin; sucralose; xanthan gum; carboxymethyl cellulose (CMC); sodium phosphate; and PROSOLV® SMCC 50M (microcrystalline cellulose and colloidal silicon dioxide).

The present invention also provides for an oral liquid suspension that includes:

| Amount (% w/v) | Component |
|---|---|
| 2.5 ± 0.25 | topiramate |
| 0.10 ± 0.01 | methylparaben |
| 0.03 ± 0.003 | sodium benzoate powder |
| 0.08 ± 0.008 | saccharin sodium dihydrate |
| 3.00 ± 0.3 | 70% solution of sorbitol |
| 2.25 ± 0.3 | propylene glycol |
| 5 ± 0.5 | glycerin (99% natural) |
| 1.26 ± 0.15 | PROSOLV® SMCC 50M (microcrystalline cellulose and colloidal silicon dioxide) |
| 0.18 ± 0.02 | sodium carboxymethyl cellulose (medium viscosity, 2% aqueous solution at 25° C. 400-800 cPs) |
| 0.18 ± 0.02 | xanthan gum NF |
| 0.20 ± 0.02 | cherry flavor, natural & artificial |
| 0.002 ± 0.0002 | FD&C Red #40 |
| 0.0002 ± 0.00002 | FD&C Yellow #6 |
| 79.67 ± 8.0 | purified water |
| 5 ± 0.5 | polyethylene glycol 400 |
| 0.25 ± 0.03 | sodium phosphate dibasic (dried) |
| 0.5 ± 0.05 | sucralose |

The composition described herein is an oral liquid suspension and not, e.g., an oral solution. As such, the active ingredient, topiramate, is not fully dissolved but is essentially suspended therein. While the active ingredient may be only slightly dissolved therein, the lack of it being fully dissolved could otherwise pose stability issues. As an oral liquid suspension, the active ingredient will typically settle to the bottom of the container during extended periods of time during the shipmen and storage. Effectively resuspending the active ingredient will need to be carried out prior to use. Additionally, the active ingredient (topiramate) is unpleasant tasting.

The composition described herein is an oral liquid suspension that includes a suspending agent, viscosifying agent, anticaking agent, and redispersing agent. Achieving a suitable stability of the suspended active ingredient is achieved in part by modifying the pH of the composition. Achieving a suitable stability of the suspended active ingredient is also achieved in part by controlling the particle sire distribution as well as the water content of the active ingredient. Including a suitable flavoring agent provides a composition that is relatively pleasant tasting. The oral liquid suspension, compared to the solid oral dosage form (e.g., tablets) containing topiramate, is therefore (i) convenient to use, (ii) has a relatively quick onset of action, (iii) can be used with children and the elderly who often have difficulties swallowing, and (iv) the dose can readily be titrated. Additionally, the above is achieved while providing for an oral liquid suspension (v) having a suitable redispersibility, (vi) is relatively stable, (vii) is relatively pleasant tasting, (viii) upon shaking will be substantially devoid of lumps or clumps, even after long storage, (ix) possesses good pourability, (x) has good physical stability properties such as low level of sedimentation (reduced or no caking), (xi) has easy redispersion on agitation, and (xii) provides for dose uniformity during each administration.

The present invention also provides for a method for delivering topiramate to a subject in need thereof. The method includes administering to the subject an oral liquid suspension described herein.

The present invention also provides for a method for treating at least one of a neurological disorder and a mental disorder in a subject. The method includes administering to a subject suffering from the disorder an oral liquid suspension described herein.

DETAILED DESCRIPTION OF THE INVENTION

The present invention can be more readily understood by reading the following detailed description of the invention and study of the included examples.

The present invention is based, in part, upon the discovery of novel oral liquid suspensions that provide advantages when used for the in vivo delivery to a mammal of the active pharmaceutical ingredient (API) topiramate. In doing so, the present invention provides for oral liquid suspensions that provide for a suitable therapeutic index and/or lower incidence, severity, or duration of adverse reaction(s) compared to previously described dosage forms containing the active ingredient in the same amount.

The oral liquid suspensions may be used for a variety of purposes, including for the in vivo delivery of the active pharmaceutical ingredient (API) topiramate. Accordingly, the present invention further provides methods of treating diseases or disorders (e.g., neurological disorder and/or a mental disorder), such as epilepsy and/or bipolar disorder.

Relative to oral tablets or chewable dispersible tablets containing an equivalent amount of topiramate, administration of the oral liquid suspension may result in a lower incidence, severity, and/or duration of adverse reactions including at least one of dizziness, headache, diplopia, ataxia, nausea, blurred vision, somnolence, rhinitis, pharyngitis, rash, vomiting, infection, fever, accidental injury, diarrhea, abdominal pain, tremor, insomnia, somnolence, backpain, fatigue, abdominal pain, and xerostomia.

In forming an oral liquid suspension, any one or more of the excipients employed can effectively be dissolved or dispersed therein (e.g., in the solvent). This includes, e.g., salts, such as sodium benzoate, saccharin sodium, and sodium carboxymethyl cellulose. In doing so, the salt can dissociate into the respective anion and cation, and would therefore no longer necessarily exist in the salt form— benzoic acid, saccharin, and carboxymethyl cellulose. However, within the context of the invention, it is appreciated that those of skill in the art understand and agree that reference to the oral liquid suspension as containing the salt form is otherwise acceptable and appropriate.

Likewise, in specific embodiments, topiramate: (having a specified particle size distribution (PSD)) can be employed in the manufacture of the oral liquid suspension. In forming the oral liquid suspension, the topiramate present therein can effectively be suspended and/or dissolved therein (e.g., in the solvent). In doing so, the topiramate would therefore no longer necessarily retain the PSD. However, within the context of the invention, it is appreciated that those of skill in the art understand and agree that reference to the oral liquid suspension as containing the topiramate as having a specified PSD (based on the topiramate employed) is otherwise acceptable and appropriate. Alternatively, reference to the oral liquid suspension as containing the topiramate as having a specified PSD (based on the topiramate present in the oral liquid suspension) is also acceptable and appropriate. As such, the PSD of the topiramate employed is often a parameter for the PSD of topiramate present in the oral liquid suspension.

As used herein, "oral liquid suspension comprising" or "oral liquid suspension that includes" refers to an oral liquid suspension manufactured from the specified ingredients. While the oral liquid suspension may include such ingredients, it is appreciated that those of skill in the art understand that one or more of the specified substances may not exist in that form, within the oral liquid suspension. However, reference to the oral liquid suspension as containing that substance is otherwise acceptable. By way of illustration, a powder may fully dissolve in the oral liquid suspension. As such, the powder form may no longer exist in the oral liquid suspension. However, reference to the oral liquid suspension as containing a powder is readily understood by the skilled artisan.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "excipient" refers to a pharmacologically inactive component present in the oral liquid suspension. Excipients include, e.g., preservatives, sweetening agents, solvents, anticaking agents, viscosity-increasing agents, suspending agents, acidifying agents, taste-masking agents, flavoring agents, and colorants. The excipients used in preparing the oral liquid suspension described herein are safe and non-toxic. Suitable excipients are disclosed in Handbook of Pharmaceutical Excipients, Rowe et al., Eds., 8th Edition, Pharmaceutical Press (2017).

One or more excipients employed in the oral liquid suspensions described herein can have a single use. For example, when present in the oral liquid suspension described herein, methylparaben can function as a preservative; saccharin sodium dihydrate powder, sucralose, and sorbitol can each function as a sweetening agent; topirimate can function as an active pharmaceutical ingredient (API); sodium benzoate can function as a preservative; disodium phosphate can function as a pH modifying agent; cherry flavor (natural and artificial) can function as a flavoring agent; and/or FD&C red #40 and FD&C yellow #6 can function as a colorant.

Additionally, one or more excipients employed in the oral liquid suspensions described herein can have a single, or multiple uses. For example, microcrystalline cellulose can function as a suspending agent, texturizer, anti-caking agent, or any combination thereof; propylene glycol can function as a preservative, solvent, viscosity-increasing agent, or any combination thereof; polyethylene glycol can function as a solvent, viscosity-increasing agent, suspending agent, or any combination thereof; glycerin can function as a preservative, sweetening agent, solvent, viscosity-increasing agent, or any combination thereof; and/or xanthan gum can function as a viscosity-increasing agent, suspending agent, or a combination thereof.

In specific embodiments, the present invention provides for an oral liquid suspension that includes topirimate, preservative, sweetener, solvent, anticaking agent, viscosifying agent, suspending agent, pH adjuster, and taste-masking agent. It is contemplated that one or more excipients can be employed in the oral liquid suspension to effectively serve multiple functions. Specifically, a single excipient can function as a preservative, solvent, and viscosity-increasing agent. Further, a single excipient can function as a preservative, sweetening agent, solvent, and viscosity-increasing agent. Excipients useful in the oral liquid suspensions described herein, having multiple functions, are described in Handbook of Pharmaceutical Excipients, Rowe et al., Eds., 8th Edition, Pharmaceutical Press (2017).

The term "preservative" refers to a substance that is added to products, such as oral liquid suspensions, to prevent decomposition by microbial growth or by undesirable chemical changes. In general, preservation is implemented in two modes, chemical and physical. Suitable preservatives include, e.g., one or more of ethanol, benzoic acid, benzyl alcohol, bronopol, butylated hydroxyanisole (BHA), butylparaben, calcium acetate, calcium chloride, calcium lactate, cetrimide, cetylpyridinium chloride, chlorhexidine, chlorobutanol, chlorocresol, chloroxylenol, citric acid monohydrate, ethylparaben, glycerin, hexetidine, imidurea, isopropyl alcohol, lactic acid, methylparaben, monothioglycerol, parabens, pentetic acid, phenoxyethanol, phenylethyl alcohol, potassium benzoate, potassium metabisulfite, potassium sorbate, propionic acid, propyl gallate, propylene glycol, propylparaben, propylparaben sodium, sodium acetate, sodium benzoate, sodium borate, sodium lactate, sodium metabisulfite, sodium propionate, sodium sulfite, sorbic acid, sulfobutyl ether ß-cyclodextrin, edetic acid, thimerosal, and xanthan.

The term "sweetening agent" or "sweetener" refers to a substance that is added to products, such as oral liquid suspensions, to provide a sweet taste like that of sugar. The sweetener can include, e.g., one or more of acesulfame potassium, alitame, aspartame, dextrose, erythritol, fructose, glycerin, isomalt, lactitol, glucose, maltitol, maltose, mannitol, monk fruit extract, neohesperidin dihydrochalcone, neotame, saccharin, saccharin sodium, sodium cyclamate, sorbitol, stevia, sucralose, sucrose, tagatose, thaumatin, trehalose, and xylitol.

The term "solvent" refers to a substance that is added to products, such as oral liquid suspensions, to dissolve the active pharmaceutical ingredient (API) and/or excipients. The solvent can include, e.g., one or more of albumin, ethanol, almond oil, benzyl alcohol, benzyl benzoate, butylene glycol, castor oil, corn oil (maize), cottonseed oil, dimethyl ether, dimethylacetamide, ethyl lactate, ethyl oleate, glycerin, isopropyl alcohol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl castor oil, propylene carbonate, propylene glycol, pyrrolidone, safflower oil, sesame oil, soybean oil, sunflower oil, triacetin, tricaprylin, triethanolamine, triethyl citrate, triolein, and water.

The term "anticaking agent" refers to a substance that is added to products, such as oral liquid suspensions, to prevent or decrease the occurrence of agglomeration of particles, such as the active pharmaceutical ingredient (API) and/or excipients. The anticaking agent is added to prevent or decrease the formation of lumps (caking), which provides for ease in packaging, transport, flowability, and consumption. The anticaking, agent can include, e.g., one or more of tribasic calcium phosphate, calcium silicate, colloidal silicon dioxide, hydrophobic colloidal silica, magnesium oxide, magnesium silicate, magnesium trisilicate, and talc.

The term "viscosity-increasing agent" refers to a substance that is added to products, such as oral liquid suspensions, to increase the viscosity. The viscosity increasing agent is used in order to impart an appropriate viscosity to the oral liquid suspension. The viscosity increasing agent increases the viscosity of the oral liquid suspension without substantially changing its other properties. The viscosity-increasing agent can include, e.g, one or more of acacia, agar, alginic acid, bentonite, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, guar gum, hectorite, hydrogenated vegetable oil type I, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, polydextrose, polyethylene glycol, polyvinyl alcohol, potassium chloride, povidone, propylene glycol alginate, saponite, sodium alginate, sodium chloride, starch, stearyl alcohol, sucrose, sulfobutyl ether ß-cyclodextrin, tragacanth, and xanthan gum.

The term "suspending agent" refers to a substance that helps the active pharmaceutical ingredient (API) stay suspended in the oral liquid suspension and prevents caking at the bottom of the container. One of the properties of a well-formulated oral liquid suspension is that it can be easily re-suspended by the use of moderate agitation or shaking. The suspending agent can include, e.g., one or more of acacia, agar, alginic acid, bentonite, calcium stearate, carbomers, carboxymethylcellulose calcium, carboxymethylcellulose sodium, carrageenan, powdered cellulose, cellulose, microcrystalline cellulose, carboxymethylcellulose sodium, ceratonia, colloidal silicon dioxide, dextrin, gelatin, guar gum, hectorite, hydrophobic colloidal silica, hydroxyethyl cellulose, hydroxyethylmethyl cellulose, hydroxypropyl cellulose, hypromellose, kaolin, magnesium aluminum silicate, maltitol solution, medium-chain triglycerides, methylcellulose, silicified microcrystalline cellulose, phospholipids, polycarbophil, polyethylene glycol, polyoxyethylene sorbitan fatty acid esters, potassium alginate, povidone, propylene glycol alginate, saponite, sesame oil, sodium alginate, sodium starch glycolate, sorbitan esters, sucrose, tragacanth, vitamin E polyethylene glycol succinate, and xanthan gum. Additionally, the suspending agent can include, e.g., PROSOLV® SMCC 50M (microcrystalline cellulose and colloidal silicon dioxide).

The suspending agent is able to reduce the formation of topiramate hydrate. In some embodiments, less than about 8 wt. %, less than about 5 wt. %, less than about 3 wt. %, less than about 1 wt. %, or less than about 0.5 wt. % of the topiramate thereof is converted into its hydrate form over the period of time of manufacturing, shipping, and storage of the oral liquid suspension described herein (e.g., up to 6-9 months) under ambient conditions.

The suspending agent also contributes to the stability of the suspension after reconstitution. In some embodiments, less than about 5 wt. %, less than about 3 wt. %, less than about 1 wt. %, less than about 0.5 wt. %, less than about 0.2 wt. %, or less than about 0.1 wt. % of the topiramate is decomposed over the period of time of manufacturing, shipping, and storage of the oral liquid suspension described herein (e.g., up to 6-9 months) under ambient conditions.

The term "acidifying agent" refers to a substance that is added to products, such as oral liquid suspensions, to lower the pH, or is added to achieve a desired pH that is lower than it would otherwise be in the absence of the acidifying agent. The acidifying agent can include, e.g., one or more of sodium phosphate dibasic, adipic acid, ammonium chloride, citric acid monohydrate, diluted hydrochloric acid, lactic acid, propionic acid, and tartaric acid.

The term "flavoring agent" refers to a substance that gives another substance flavor, altering the characteristics of the solute, causing it to become sweet, sour, tangy, etc. A flavor is a quality of something that affects the sense of taste. The flavoring agent can include, e.g., cherry flavor, grape, or peppermint.

The term "colorant" or "coloring agent" refers to substance that is added or applied in order to change the color of a material or surface. Colorants work by absorbing varying amounts of light at different wavelengths (or frequencies) of its spectrum, transmitting (if translucent) or reflecting the remaining light in straight lines or scattered. The colorant can include, e.g., FD&C red #40, FD&C yellow #6, or a combination thereof.

The term "oral liquid suspension" refers to a pharmaceutical dosage form that is a liquid and is orally administered. It includes topiramate mixed with a liquid vehicle for oral administration. Being a suspension, the dosage form consists of undissolved particles (e.g., topiramate and/or excipients). The undissolved particles can be suspended in the oral liquid suspension. Alternatively, the undissolved particles can settle to the bottom of the container where it can be shaken and/or agitated to resuspend in the solution.

The term "topiramate" refers to the compound chemically designated as 2,3:4,5-Di-O-isopropylidene-β-D-fructopyranose sulfamate. Topiramate has the molecular formula $C_{12}H_{21}NO_8S$ and a molecular weight of 339.36. In specific embodiments, the topiramate functions as the sole active ingredient. The topiramate used herein will also have a suitable particle size distribution (PSD). Topiramate, unless otherwise specified, includes the free base, pharmaceutically acceptable salts thereof, isomers, and polymorphs thereof. Topiramate is commercially available in multiple physical forms (e.g., amorphous or crystalline forms). A micronized amorphous form is commercially available from Polpharma (Poland).

The term "glycerin" or "glycerol" refers to the compound chemically designated as propane-1,2,3-triol, having the chemical formula $C_3H_8O_3$ and molar mass 92.094 g/mol. The glycerin can be glycerin, 99% natural. When present in the oral liquid suspension described herein, the glycerin can function as a preservative, sweetening agent, solvent, viscosity-increasing agent, or any combination thereof.

The term "propylene glycol" refers to the compound chemically designated as propane-1,2-diol, having the chemical formula $C_3H_8O_2$, and molar mass 76.095 g/mol. When present in the oral liquid suspension described herein, the propylene glycol can function as a preservative, solvent, viscosity-increasing agent, or any combination thereof.

The term "polyethylene glycol" or "PEG" refers to the compound chemically designated as polyoxyethylene) or PEO (also referred to as polyethylene oxide or PEO), having the chemical formula $C_{2n}H_{4n+2}O_{n+1}$, and molar mass 18.02+44.05n g/mol. PEG, PEO, and POE refer to an oligomer or polymer of ethylene oxide. The three names are chemically synonymous, but historically PEG is preferred in the biomedical field, whereas PEO is more prevalent in the field of polymer chemistry. Because different applications require different polymer chain lengths, PEG has tended to refer to oligomers and polymers with a molecular mass below 20,000 g/mol, PEO to polymers with a molecular mass above 20,000 g/mol, and POE to a polymer of any molecular mass. PEGs are typically prepared by polymerization of ethylene oxide and are commercially available over a wide range of molecular weights from 300 g/mol to 10,000,000 g/mol. When present in the oral liquid suspension described herein, the polyethylene glycol can function as a solvent, viscosity-increasing agent, suspending agent, or any combination thereof.

The polyethylene glycol can be polyethylene glycol 400. The term "polyethylene glycol 400" refers to a low-molecular-weight grade of polyethylene glycol, having the chemical formula $C_{2n}H_{4n+2}O_{n+1}$, wherein n=8.2 to 9.1, and molar mass 380-420 g/mol. When present in the oral liquid suspension described herein, the polyethylene glycol 400 can function as a solvent, viscosity-increasing agent, suspending agent, or any combination thereof.

The term "methylparaben" refers to the compound chemically designated as methyl 4-hydroxybenzoate, having the chemical formula $C_8H_8O_3$, and molar mas 152.149 g/mol. When present in the oral liquid suspension described herein, the methylparaben can function as a preservative.

The term "sodium benzoate" refers to the compound benzoate of soda, having the chemical formula $C_7H_5NaO_2$, and molar mass 144.105 g/mol. When present in the oral liquid suspension described herein, the sodium benzoate can function as a preservative.

The term "sorbitol" refers to the compound chemically designated as (2S,3R,4R,5R)-hexane-1,2,3,4,5,6-hexol, having the chemical formula $C_6H_{14}O_6$, and molar mass 182.17 g/mol. The sorbitol can be solid sorbitol. Alternatively, the sorbitol can be in solution (e.h., 70% solution of sorbitol). When present in the oral liquid suspension described herein, the sorbitol can function as a sweetening agent.

The term "saccharin" refers to the compound chemically designated as 1,1-dioxo-1,2-benzothiazol-3-one, having the chemical formula $C_7H_5NO_3S$, and molar mass 183.18 g/mol. When present in the oral liquid suspension described herein, the saccharin can function as a sweetening agent.

The saccharin can be saccharin sodium dihydrate powder. The term "saccharin sodium" refers to the sodium salt of saccharin. When present in the oral liquid suspension described. herein, the saccharin sodium dihydrate powder can function as a sweetening agent.

The term "sucralose" refers to the compound chemically designated as 1,6-dichloro-1,6-dideoxy-β-D-fructofuranosyl-4-chloro-4-deoxy-α-D-galactopyranoside, having the chemical formula $C_{12}H_{19}Cl_3O_8$, and molar mass 397.64 g/mol. When present in the oral liquid suspension described herein, the sucralose can function as a sweetening agent.

The term "citric acid" refers to the compound chemically designated as 2-hydroxypropane-1,2,3-tri carboxylic acid, having the chemical formula $C_6H_8O_7$, and molar mass 192.123 g/mol (anhydrous) or 210.038 g/mol (monohydrate). When present in the oral liquid suspension described herein, the citric acid can function as an acidifying agent, preservative, or combination thereof.

The term "xanthan gum" refers to a polysaccharide having the CAS Number 11138-66-2, and chemical formula $C_{35}H_{49}O_{29}$ (monomer). When present in the oral liquid suspension described herein, the xanthan gum can function as a viscosity-increasing agent, suspending agent, or a combination thereof.

The term "carboxymethyl cellulose," "carmellose," or "CMC" refers to a cellulose derivative with carboxymethyl groups (—CH$_2$—COOH) bound to some of the hydroxyl groups of the glucopyranose monomers that make up the cellulose backbone. It is often used as its sodium salt, sodium carboxymethyl cellulose. CMC has the CAS Number 9000-11-7. The carboxymethyl cellulose can be sodium carboxymethyl cellulose (medium viscosity, 2% aqueous solution at 25° C. 400-800 cPs). When present in the oral liquid suspension described herein, the carboxymethyl cellulose can function as a viscosity-increasing agent, suspending agent, or combination thereof.

The term "microcrystalline cellulose" or "MCC" is a term for refined wood pulp. A naturally occurring polymer, it is composed of glucose units connected by a 1-4 beta glycosidic bond. These linear cellulose chains are bundled together as microfibril spiraled together in the walls of plant cell. When present in the oral liquid suspension described herein, the microcrystalline cellulose can function as a suspending agent.

The term "silicified microcrystalline cellulose" refers to MCC which is silicified. Silicification is the process in which organic matter becomes saturated with silica. When present in the oral liquid suspension described herein, the silicified microcrystalline cellulose can function as a suspending agent.

The term "disodium phosphate" or "DSP" or "sodium hydrogen phosphate" or "sodium phosphate dibasic" refers to the inorganic compound with the formula $Na_2HPO_4$. and CAS Number 7558-79-4. The disodium phosphate can be sodium phosphate dibasic (dried). When present in the oral liquid suspension described herein, the disodium phosphate can function as a pH modifying agent.

The term "PROSOLV® SMCC" refers to silicified microcrystalline cellulose, which is a combination of microcrystalline cellulose (MCC) and colloidal silicon dioxide (CSD). The commercial product PROSOLV® SMCC 50M has an average particle size determined by laser diffraction (μm) of 65. The commercial product PROSOLV® SMCC 50M also has a bulk density (g/mL) of 0.25-0.37. PROSOLV® SMCC is commercially available from JRS Pharma (Patterson, N.Y.), https://www.jrspharma.comlpharma_en/.

The term "neurological disorder" refers to any disorder of the nervous system. Structural, biochemical or electrical abnormalities in the brain, spinal cord or other nerves can result in a range of symptoms. Such disorders may be diagnosed by a health care professional.

The term "mental disorder" or "psychiatric disorder" refers to a behavioral or mental pattern that causes significant distress or impairment of personal functioning. Such features may be persistent, relapsing and remitting, or occur as a single episode. Many disorders have been described, with signs and symptoms that vary widely between specific disorders. Such disorders may be diagnosed by a mental health professional. The Diagnostic and Statistical Manual of Mental Disorders, Fifth Edition ("DSM-5") is the 2013 update to the Diagnostic and Statistical Manual of Mental Disorders, the taxonomic and diagnostic tool published by the American Psychiatric Association (APA). In the United States, the DSM serves as the principal authority for psychiatric diagnoses. Treatment recommendations are often determined by DSM classifications.

The term "epilepsy" refers to a group of neurological disorders characterized by epileptic seizures. Epileptic seizures are episodes that can vary from brief and nearly undetectable periods to long periods of vigorous shaking. These episodes can result in physical injuries, including occasionally broken bones. In epilepsy, seizures tend to recur and, as a rule, have no immediate underlying cause. Isolated seizures that are provoked by a specific cause such as poisoning are not deemed to represent epilepsy. People with epilepsy may be treated differently in various areas of the world and experience varying degrees of social stigma due to their condition.

The term "focal seizures" or "partial seizures" or "partial onset seizures" refer to localized seizures and are seizures which affect initially only one hemisphere of the brain. The brain is divided into two hemispheres, each consisting of four lobes—the frontal, temporal, parietal and occipital lobes. A focal seizure is generated in and affects just one part of the brain—a whole hemisphere or part of a lobe. Symptoms will vary according to where the seizure occurs. In the frontal lobe symptoms may include a wave-like sensation in the head; in the temporal lobe, a feeling of déjà vu; in the parietal lobe, numbness or tingling; and in the occipital lobe, visual disturbance or hallucination.

The term "generalized seizures," as opposed to focal seizures, refer to a type of seizure that impairs consciousness and distorts the electrical activity of the whole or a larger portion of the brain (which can be seen, for example, on electroencephalography, EEG.

The term "generalized tonic-clonic seizure" or "grand mal seizure" refers to a type of generalized seizure that produces bilateral, convulsive tonic and clonic muscle contractions. Tonic-clonic seizures are the seizure type most commonly associated with epilepsy and seizures in general and the most common seizure associated with metabolic imbalances. A tonic-clonic seizure is a convulsion that combines the characteristics of tonic (meaning stiffening) and clonic (meaning rhythmical jerking) seizures. The disturbance in functioning is present in both sides of the brain. The tonic phase comes first (e.g., all the muscles stiffen, air being forced past the vocal cords causes a cry or groan, and the person loses consciousness and falls to the floor). After the tonic phase comes the clonic phase (e.g., the arms and usually the legs begin to jerk rapidly and rhythmically, bending and relaxing at the elbows, hips, and knees, and after a few minutes, the jerking slows and stops.).

The term "Lennox-Gastaut syndrome" refers to a complex, rare, and severe childhood-onset epilepsy. It is characterized by multiple and concurrent seizure types, cognitive dysfunction, and slow spike waves on electroencephalogram (EEG). Typically, it presents in children aged 3-5 years and can persist into adulthood. It has been associated with several gene mutations, perinatal insults, congenital infections, brain humors/malformations, and genetic disorders such as tuberous sclerosis and West syndrome.

The term "generalized seizures of Lennox-Gastaut syndrome" refers to generalized seizures associated with Lennox-Gastaut syndrome.

The term "antiepileptic drug," "anticonvulsant," or "AED" refers to a diverse group of pharmacological agents used in the treatment of epileptic seizures. Anticonvulsants are also increasingly being used in the treatment of bipolar disorder and borderline personality disorder, since many seem to act as mood stabilizers, and for the treatment of neuropathic pain. Anticonvulsants suppress the excessive rapid firing of neurons during seizures. Anticonvulsants also prevent the spread of the seizure within the brain.

The term "bipolar disorder," previously known as manic depression, refers to a mental disorder that causes periods of depression and periods of abnormally elevated mood. The elevated mood is significant and is known as mania or hypomania, depending on its severity, or whether symptoms of psychosis are present. During mania, an individual behaves or feels abnormally energetic, happy, or irritable. Individuals often make poorly thought out decisions with little regard to the consequences. The need for sleep is usually reduced during manic phases. During periods of depression, there may be crying, a negative outlook on life, and poor eye contact with others.

The term "combination therapy," "adjunctive therapy," or "polytherapy" refers to therapy that uses more than one medication or modality (versus "monotherapy," which is any therapy taken alone). Typically, these terms refer to using multiple therapies to treat a single disease, and often all the therapies are pharmaceutical (although it can also involve non-medical therapy, such as the combination of medications and talk therapy to treat depression). Monotherapy can be applied to any therapeutic approach, but it is most commonly used to describe the use of a single medication. Typically, monotherapy is selected because a single medication is adequate to treat the medical condition. However, monotherapies may also be used because of unwanted side effects or dangerous drug interactions.

The particle size of topiramate can be measured by suitable techniques such as laser light scattering (e.g. Malvern Light Scattering), Coulter counter, microscopy, Fraunhofer diffraction and any other technique known in the art. This particle size can be obtained either by the final step during the manufacture of the topiramate or by the use of conventional micronizing techniques after the crystallization procedure(s).

The term "$T_{max}$" refers to time of maximum plasma concentration and is the time to reach maximum (peak) plasma concentration following drug administration, It is measured in units of time (hours).

The term "$t_{1/2}$" refers to elimination half-life and is time to reach elimination half-life (to be used in one or non-compartmental model). It is measured in units of time (hours).

The term "stable" refers to chemical stability, wherein not more than 5 wt. % of total related substances are formed on storage at 40° C. and 75% relative humidity (R.H.) for a period of 90 days.

The term "shaken" refers to shaken prior to use. For example, a medical practitioner or subject (e.g., patient) can shake the oral liquid suspension prior to administration. The shaking can include vigorously shaking by hand, for example, for about 5 to 40 seconds.

The term "release," "released," "releasing," and the like, when used in connection with a pharmaceutical dosage form, refers to the process or the portion of the active ingredient that leaves the dosage form following contact with an aqueous environment. Unless otherwise indicated, the quantity of an active ingredient released from a dosage form is measured by dissolution testing in water as described in this invention. The results of the dissolution testing are reported as a percentage (w/w) released as a function of time or as the release time, in some embodiments, complete release of an active ingredient occurs when at least 90% of the active ingredient has been released from the dosage form.

The term "immediate-release" refers to those which disintegrate rapidly and/or get dissolved to release the medicaments or active ingredient.

The term "sedimentation volume ratio" or "sedimentation ratio" refers to a ratio of the ultimate volume of sediment (Vu) to the original volume of sediment (VO) before settling. The sedimentation volume ratio is generally achieved within about 5 minutes, 3 minutes, 2 minutes, 60 seconds, 45 seconds, or 30 seconds after the powder formulation is reconstituted to the suspension. Various mechanical means, such as shaking, swirling, heating, or any combination thereof can be used to promote a uniform suspension.

The term "subject" refers to a mammal, such as an animal or a human. Hence, the methods disclosed herein can be useful in human therapy and veterinary applications. In one embodiment, the subject is an animal. In another embodiment, the subject is a human.

The term "treat" or "treating" refers to attain or attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a patient suffering from the condition, decreasing the dose of another medication required to treat the condition, enhancing the effect of another medication a patient is taking for the condition, and prolonging the survival of a patient having the condition.

The term "$D_{90}$" refers to the particle size corresponding to 90% of the cumulative undersize distribution by volume.

The term "$D_{50}$" refers to the particle size corresponding to 50% of the cumulative undersize distribution by volume.

The term "$D_{10}$" refers to the particle size corresponding to 10% of the cumulative undersize distribution by volume.

It is appreciated that those of skill in the art understand that each of the excipients present in the oral liquid suspension provide for one or more functions. For example, glycerin can function as a preservative, sweetening agent, solvent, viscosity-increasing agent, or any combination thereof. Formulating an oral liquid suspension to contain excipients that provide multiple functions is beneficial and advantageous, for example, as the oral liquid suspension can have a pleasant taste and/or can have a higher drug load (thereby requiring a lower volume to be administered), while achieving the desirable physicochemical properties and technical attributes.

The viscosity can be measured by using as suitable instrument such as Brookfield viscometer, Haake VT 550 viscometer at room temperature (25° C.).

The oral liquid suspension described herein can be packaged in a suitable pack/container such as amber colored polyethylene terephthalate (PET) bottle, glass bottle, high density polyethylene (DPE) bottle, low density polyethylene (LDPE) bottle, polypropylene (PP) bottle, the like. The glass or plastic bottle can be provided with a child proof closure. The package can include a syringe or cup (marked in mL, ounces, or both) for ease of dosing. The container such as bottle has a fill volume of, e.g., from about 50 mL to about 500 mL containing the topiramate oral liquid suspension. Containers for use in the storage of the oral suspensions may be used to administer a multiple dose of topiramate.

Specific Ranges, Values, Features, and Embodiments

The specific embodiments provided below describing the ranges, values, and features are for illustration purposes only, and do not otherwise limit the scope of the disclosed subject matter, as defined by the claims.

In specific embodiments, the oral liquid suspension includes topiramate, present in 2.5±0.30% (w/v).

In specific embodiments, the oral liquid suspension includes topiramate, present in 2.5±0.25% (w/v).

In specific embodiments, the oral liquid suspension includes topiramate, present in 2.5±0.20% (w/v).

In specific embodiments, the oral liquid suspension includes topiramate, present in 2.5±0.15% (w/v).

In specific embodiments, the oral liquid suspension includes topiramate, present in 2.5±0.10% (w/v).

In specific embodiments, the oral liquid suspension includes topiramate, present in 2.5±0.05% (w/v).

In specific embodiments, the oral liquid suspension includes topiramate, present in 25 mg per milliliter.

In specific embodiments, the oral liquid suspension includes topiramate, present in 25±2.5 mg per milliliter.

In specific embodiments, the oral liquid suspension includes topiramate, present in 25±2.0 mg per milliliter.

In specific embodiments, the oral liquid suspension includes topiramate, present in 25±1.5 mg per milliliter.

In specific embodiments, the oral liquid suspension includes topiramate, present in 25±1.0 mg per milliliter.

In specific embodiments, the oral liquid suspension includes topiramate, present in 25±0.5 mg per milliliter.

In specific embodiments, the oral liquid suspension includes one or more preservatives selected from ethanol, benzoic acid, benzyl alcohol, bronopol, butylated hydroxyanisole (BHA), butylparaben, calcium acetate, calcium chloride, calcium lactate, cetrimide, cetylpyridinium chloride, chlorhexidine, chlorobutanol, chlorocresol, chloroxylenol, citric acid monohydrate, ethylparaben, glycerin, hexetidine, imidurea, isopropyl alcohol, lactic acid, methylparaben, monothioglycerol, parabens, pentetic acid, phenoxyethanol, phenylethyl alcohol, potassium benzoate, potassium metabisulfite, potassium sorbate, propionic acid, propyl gallate, propylene glycol, propylparaben, propylparaben sodium, sodium acetate, sodium benzoate, sodium borate, sodium lactate, sodium metabisulfite, sodium propionate, sodium sulfite, sorbic acid, sulfobutyl ether ß-cyclodextrin, edetic acid, thimerosal, xanthan, and combinations thereof.

In specific embodiments, the oral liquid suspension includes one or more sweeteners selected from acesulfame potassium, alitame, aspartame, dextrose, erythritol, fructose, glycerin, isomalt, lactitol, glucose, maltitol, maltose, mannitol, monk fruit extract, neohesperidin dihydrochalcone, neotame, saccharin, saccharin sodium, sodium cyclamate, sorbitol, stevia, sucralose, sucrose, tagatose, thaumatin, trehalose, xylitol, and combinations thereof.

In specific embodiments, the oral liquid suspension includes one or more solvents selected from albumin, ethanol, almond oil, benzyl alcohol, benzyl benzoate, butylene glycol, castor oil, corn oil (maize), cottonseed oil, dimethyl ether, dimethylacetamide, ethyl lactate, ethyl oleate, glycerin, isopropyl alcohol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl castor oil, propylene carbonate, propylene glycol, pyrrolidone, safflower oil, sesame oil, soybean oil, sunflower oil, triacetin, tricaprylin, triethanolamine, triethyl citrate, triolein, water, and combinations thereof.

In specific embodiments, the oral liquid suspension includes one or more anticaking agents selected from tribasic calcium phosphate, calcium silicate, colloidal silicon dioxide, hydrophobic colloidal silica, magnesium oxide, magnesium silicate, magnesium trisilicate, talc, and combinations thereof.

In specific embodiments, the oral liquid suspension includes one or more viscosity-increasing agents selected from acacia, agar, alginic acid, bentonite, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, guar gum, hectorite, hydrogenated vegetable oil type I, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, polydextrose, polyethylene glycol, polyvinyl alcohol, potassium chloride, povidone, propylene glycol alginate, saponite, sodium alginate, sodium chloride, starch, stearyl alcohol, sucrose, sulfobutyl ether ß-cyclodextrin, tragacanth, xanthan gum, and combinations thereof.

In specific embodiments, the oral liquid suspension includes one or more suspending agents selected from acacia, agar, alginic acid, bentonite, calcium stearate, carbomers, carboxymethylcellulose calcium, carboxymethylcellulose sodium, carrageenan, powdered cellulose, cellulose, microcrystalline cellulose, carboxymethylcellulose sodium, ceratonia, colloidal silicon dioxide, dextrin, gelatin, guar gum, hectorite, hydrophobic colloidal silica, hydroxyethyl cellulose, hydroxyethylmethyl cellulose, hydroxypropyl cellulose, hypromellose, kaolin, magnesium aluminum silicate, maltitol solution, medium-chain triglycerides, methylcellulose, silicified microcrystalline cellulose, phospholipids, polycarbophil, polyethylene glycol, polyoxyethylene sorbitan fatty acid esters, potassium alginate, povidone, propylene glycol alginate, saponite, sesame oil, sodium alginate, sodium starch glycolate, sorbitan esters, sucrose, tragacanth, vitamin E polyethylene glycol succinate, and xanthan gum, PROSOLV® SMCC 50M (microcrystalline cellulose and colloidal silicon dioxide), and combinations thereof.

In specific embodiments, the oral liquid suspension includes one or more acidifying agents selected from sodium phosphate dibasic, adipic acid, ammonium chloride, citric acid monohydrate, diluted hydrochloric acid, lactic acid, propionic acid, tartaric acid, and combinations thereof.

In specific embodiments, the oral liquid suspension includes one or more flavoring agents selected from cherry flavor, grape, peppermint, and combinations thereof.

In specific embodiments, the oral liquid suspension includes water, present in 79.67±10% (w/v).

In specific embodiments, the oral liquid suspension includes water, present in 79.67±8% (w/v).

In specific embodiments, the oral liquid suspension includes water, present in 79.67±7% (w/v).

In specific embodiments, the oral liquid suspension includes water, present in 79.67±5% (w/v).

In specific embodiments, the oral liquid suspension includes water, present in 79.67±3% (w/v).

In specific embodiments, the oral liquid suspension includes water, present in 79.67±1.5% (w/v).

In specific embodiments, the oral liquid suspension includes glycerin, present in 5±2.0% (w/v).

In specific embodiments, the oral liquid suspension includes glycerin, present in 5±1.0% (w/v).

In specific embodiments, the oral liquid suspension includes glycerin, present in 5±0.75% (w/v).

In specific embodiments, the oral liquid suspension includes glycerin, present in 5±0.50% (w/v).

In specific embodiments, the oral liquid suspension includes glycerin, present in 5±0.25% (w/v).

In specific embodiments, the oral liquid suspension includes propylene glycol, present in 2.25±1.0% (w/v).

In specific embodiments, the oral liquid suspension includes propylene glycol, present in 2.25±0.75% (w/v).

In specific embodiments, the oral liquid suspension includes propylene glycol, present in 2.25±0.5% (w/v).

In specific embodiments, the oral liquid suspension includes propylene glycol, present in 2.25±0.3% (w/v).

In specific embodiments, the oral liquid suspension includes propylene glycol, present in 2.25±0.25% (w/v).

In specific embodiments, the oral liquid suspension includes polyethylene glycol 400, present in 5.00±2.0% (w/v).

In specific embodiments, the oral liquid suspension includes polyethylene glycol 400, present in 5.00±1.0% (w/v).

In specific embodiments, the oral liquid suspension includes polyethylene glycol 400, present in 5.00±0.75% (w/v).

In specific embodiments, the oral liquid suspension includes polyethylene glycol 400, present in 5.00±0.5% (w/v).

In specific embodiments, the oral liquid suspension includes polyethylene glycol 400, present in 5.00±0.25% (w/v).

In specific embodiments, the oral liquid suspension includes methylparaben, present in 0.1±0.05% (w/v).

In specific embodiments, the oral liquid suspension includes methylparaben, present in 0.1±0.04% (w/v).

In specific embodiments, the oral liquid suspension includes methylparaben, present in 0.1±0.03% (w/v).

In specific embodiments, the oral liquid suspension includes methylparaben, present in 0.1±0.02% (w/v).

In specific embodiments, the oral liquid suspension includes methylparaben, present in 0.1±0.01% (w/v).

In specific embodiments, the oral liquid suspension includes sodium benzoate powder, present in 0.03±0.006% (w/v).

In specific embodiments, the oral liquid suspension includes sodium benzoate powder, present in 0.03±0.003% (w/v).

In specific embodiments, the oral liquid suspension includes sodium benzoate powder, present in 0.03±0.002% (w/v).

In specific embodiments, the oral liquid suspension includes sodium benzoate powder, present in 0.03±0.001% (w/v).

In specific embodiments, the oral liquid suspension includes sorbitol, present in 2.1±0.42% (w/v).

In specific embodiments, the oral liquid suspension includes sorbitol, present in 2.1±0.6% (w/v).

In specific embodiments, the oral liquid suspension includes sorbitol, present in 2.1±0.5% (w/v).

In specific embodiments, the oral liquid suspension includes sorbitol, present in 2.1±0.3% (w/v).

In specific embodiments, the oral liquid suspension includes sorbitol, present in 2.1±0.2% (w/v).

In specific embodiments, the oral liquid suspension includes sorbitol, present in 2.1±0.1% (w/v).

In specific embodiments, the oral liquid suspension includes a 70% solution of sorbitol, present in 3.0±0.6% (w/v).

In specific embodiments, the oral liquid suspension includes a 70% solution of sorbitol, present in 3.0±0.4% (w/v).

In specific embodiments, the oral liquid suspension includes a 70% solution of sorbitol, present in 3.0±0.2% (w/v).

In specific embodiments, the oral liquid suspension includes a 70% solution of sorbitol, present in 3.0±0.1% (w/v).

In specific embodiments, the oral liquid suspension includes saccharin sodium dihydrate powder, present in 0.08±0.04% (w/v).

In specific embodiments, the oral liquid suspension includes saccharin sodium dihydrate powder, present in 0.08±0.02% (w/v).

In specific embodiments, the oral liquid suspension includes saccharin sodium dihydrate powder, present in 0.08±0.015% (w/v).

In specific embodiments, the oral liquid suspension includes saccharin sodium dihydrate powder, present in 0.08±0.010% (w/v).

In specific embodiments, the oral liquid suspension includes saccharin sodium dihydrate powder, present in 0.08±0.008% (w/v).

In specific embodiments, the oral liquid suspension includes saccharin sodium dihydrate powder, present in 0.08±0.003% (w/v).

In specific embodiments, the oral liquid suspension includes saccharin sodium dihydrate powder, present in 0.08±0.012% (w/v).

In specific embodiments, the oral liquid suspension includes sucralose, present in 0.5±0.15% (w/v).

In specific embodiments, the oral liquid suspension includes sucralose, present in 0.5±0.10% (w/v).

In specific embodiments, the oral liquid suspension includes sucralose, present in 0.5±0.05% (w/v).

In specific embodiments, the oral liquid suspension includes sucralose, present in 0.5±0.25% (w/v).

In specific embodiments, the oral liquid suspension includes sodium phosphate dibasic (dried), present in 0.25±0.08% (w/v).

In specific embodiments, the oral liquid suspension includes sodium phosphate dibasic (dried), present in 0.25±0.05% (w/v).

In specific embodiments, the oral liquid suspension includes sodium phosphate dibasic (dried), present in 0.25±0.03% (w/v).

In specific embodiments, the oral liquid suspension includes sodium phosphate dibasic (dried), present in 0.25±0.025% (w/v).

In specific embodiments, the oral liquid suspension includes sodium phosphate dibasic (dried), present in 0.2.5±0.02% (w/v).

In specific embodiments, the oral liquid suspension includes xanthan gum, present in 0.18±0.10%.

In specific embodiments, the oral liquid suspension includes xanthan gum, present in 0.18±0.08%.

In specific embodiments, the oral liquid suspension includes xanthan gum, present in 0.18±0.05%.

In specific embodiments, the oral liquid suspension includes xanthan gum, present in 0.18±0.03%.

In specific embodiments, the oral liquid suspension includes xanthan gum, present in 0.18±0.02%.

In specific embodiments, the oral liquid suspension includes sodium carboxymethyl cellulose (medium viscosity, 2% aqueous solution at 25° C. 400-800 cPs), present in 0.18±0.10% (w/v).

In specific embodiments, the oral liquid suspension includes sodium carboxymethyl cellulose (medium viscosity, 2% aqueous solution at 25° C. 400-800 cPs), present in 0.18±0.08% (w/v).

In specific embodiments, the oral liquid suspension includes sodium carboxymethyl cellulose (medium viscosity, 2% aqueous solution at 25° C. 400-800 cPs), present in 0.18±0.05% (w/v).

In specific embodiments, the oral liquid suspension includes sodium carboxymethyl cellulose (medium viscosity, 2% aqueous solution at 25° C. 400-800 cPs), present in 0.18±0.04% (w/v).

In specific embodiments, the oral liquid suspension includes sodium carboxymethyl cellulose (medium viscosity, 2% aqueous solution at 25° C. 400-800 cPs), present in 0.18±0.02% (w/v).

In specific embodiments, the oral liquid suspension includes PROSOLV® SMCC 50M (microcrystalline cellulose and colloidal silicon dioxide), present in 1.26±0.5% (w/v).

In specific embodiments, the oral liquid suspension includes PROSOLV® SMCC 50M (microcrystalline cellulose and colloidal silicon dioxide), present in 1.26±0.4% (w/v).

In specific embodiments, the oral liquid suspension includes PROSOLV® SMCC 50M (microcrystalline cellulose and colloidal silicon dioxide), present in 1.26±0.3% (w/v).

In specific embodiments, the oral liquid suspension includes PROSOLV® SMCC 50M (microcrystalline cellulose and colloidal silicon dioxide), present in 1.26±0.2% (w/v).

In specific embodiments, the oral liquid suspension includes PROSOLV® SMCC 50M (microcrystalline cellulose and colloidal silicon dioxide), present in 1.26±0.1% (w/v).

In specific embodiments, the oral liquid suspension includes one or more flavoring agents.

In specific embodiments, the oral liquid suspension includes the flavoring agent cherry flavor, natural & artificial.

In specific embodiments, the oral liquid suspension does not include a flavoring agent.

In specific embodiments, the oral liquid suspension includes one or more colorants.

In specific embodiments, the oral liquid suspension includes the colorants FD&C Red #40 and FD&C Yellow #6.

In specific embodiments, the oral liquid suspension does not include a colorant.

In specific embodiments, the oral liquid suspension includes:

| Amount (% w/v) | Component |
|---|---|
| 2.5 ± 0.25 | topiramate |
| 0.10 ± 0.01 | methylparaben |
| 0.03 ± 0.003 | sodium benzoate powder |
| 0.08 ± 0.008 | saccharin sodium dihydrate |
| 3.00 ± 0.3 | 70% solution of sorbitol |
| 2.25 ± 0.3 | propylene glycol |
| 5 ± 0.5 | glycerin (99% natural) |
| 1.26 ± 0.15 | PROSOLV ® SMCC 50M (microcrystalline cellulose and colloidal silicon dioxide) |
| 0.18 ± 0.02 | sodium carboxymethyl cellulose (medium viscosity, 2% aqueous solution at 25° C. 400-800 cPs) |
| 0.18 ± 0.02 | xanthan gum NF |
| 0.20 ± 0.02 | cherry flavor, natural & artificial |
| 0.002 ± 0.0002 | FD&C Red #40 |
| 0.0002 ± 0.00002 | FD&C Yellow #6 |
| 79.67 ± 8.0 | purified water |
| 5 ± 0.5 | polyethylene glycol 400 |
| 0.25 ± 0.03 | sodium phosphate dibasic (dried) |
| 0.5 ± 0.05 | sucralose |

In specific embodiments, the oral liquid suspension has a volume of up to 50 mL.

In specific embodiments, the oral liquid suspension has a volume of up to 20 mL.

In specific embodiments, the oral liquid suspension has a volume of 0.2 mL to 20 mL.

In specific embodiments, the oral liquid suspension has a volume of 0.2 mL, 0.5 mL, 2.5 mL, 10 mL, 15 mL, or 20 mL.

In specific embodiments, the oral liquid suspension has a volume of 0.2 mL.

In specific embodiments, the oral liquid suspension has a volume of 0.5 mL.

In specific embodiments, the oral liquid suspension has a volume of 2.5 mL.

In specific embodiments, the oral liquid suspension has a volume of 10 mL.

In specific embodiments, the oral liquid suspension has a volume of 15 mL.

In specific embodiments, the oral liquid suspension has a volume of 20 mL.

In specific embodiments, the oral liquid suspension has a pH of 7.5-7.9.

In specific embodiments, the oral liquid suspension has a pH of 7.7±0.1.

In specific embodiments, the oral liquid suspension has a viscosity (at 25° C.) of 300-400 mPs.

In specific embodiments, the oral liquid suspension has a viscosity (at 25° C.) of 310-390 mPs.

In specific embodiments, the oral liquid suspension has a viscosity (at 25° C.) of 320-380 mPs.

In specific embodiments, the oral liquid suspension has a viscosity (at 25° C.) of 325-375 mPs.

In specific embodiments, the oral liquid suspension has a viscosity (at 25° C.) of 341.7±20 mPs.

In specific embodiments, the oral liquid suspension has a viscosity (at 25° C.) of 341.7±10 mPs.

In specific embodiments, the oral liquid suspension has a viscosity (at 25° C.) of 341.7±5 mPs.

In specific embodiments, the oral liquid suspension has a specific gravity of not greater than 1.3.

In specific embodiments, the oral liquid suspension has a specific gravity of not greater than 1.25.

In specific embodiments, the oral liquid suspension has a specific gravity of not greater than 1.2.

In specific embodiments, the oral liquid suspension has a specific gravity of not greater than 1.05.

In specific embodiments, the oral liquid suspension has a specific gravity of not greater than 1.049.

In specific embodiments, the oral liquid suspension is packaged in a container.

In specific embodiments, the oral liquid suspension is packaged in an amber colored polyethylene terephthalate (PET) bottle.

In specific embodiments, the oral liquid suspension is packaged in a glass bottle.

In specific embodiments, the oral liquid suspension is packaged in a high density polyethylene (HDPE) bottle.

In specific embodiments, the oral liquid suspension is packaged in a low density polyethylene (LDPE) bottle.

In specific embodiments, the oral liquid suspension is packaged in a polypropylene (PP) bottle.

In specific embodiments, the oral liquid suspension is packaged in a glass or plastic bottle with a child proof closure.

In specific embodiments, the oral liquid suspension is packaged in a glass or plastic bottle and the packaging further includes a syringe or cup, marked in mL, ounces, or both.

In specific embodiments, the oral liquid suspension is packaged in a glass or plastic bottle configured for use to administer multiple doses of topiramate.

In specific embodiments, the oral liquid suspension, while packaged in a container, is free from microbial contamination for a specified period of time (e.g., ≥20 days, ≥30 days, ≥60 days, ≥90 days, ≥180 days, ≥12 months, or ≥24 months) when tested according to <1111>USP-30 NF-25.

In specific embodiments, the oral liquid suspension, while packaged in a container, is free from microbial contamination for an extended period of time encountered with the shipping and storage of the oral liquid suspension.

In specific embodiments, the oral liquid suspension, while packaged in a container, is free from microbial contamination for an extended period of time encountered with the shipping and storage of the oral liquid suspension under ambient conditions, wherein the microbial contamination includes *Escherichia coli* (*E. coli*).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.1 wt. % *Escherichia coli* (*E. coli*).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.01 wt. % *Escherichia coli* (*E. coli*).

In specific embodiments, the oral liquid suspension, while packaged in a container, is free from microbial contamination for an extended period of time encountered with the shipping and storage of the oral liquid suspension under ambient conditions, wherein the microbial contamination includes *Burkholderia cepacia* complex (BCC), In specific embodiments, the oral liquid suspension, while packaged in a container, is free from microbial contamination for an extended period of time encountered with the shipping and storage of the oral liquid suspension under ambient conditions, wherein the microbial contamination includes less than 0.1 wt. % *Burkholderia cepacia* complex (BCC).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.01 wt. % Burkholderia cepacia complex (BCC).

In specific embodiments, the oral liquid suspension, while packaged in a container, is free from microbial contamination for at least 24 months under ambient conditions.

In specific embodiments, the oral liquid suspension, while packaged in a container, is free from microbial contamination for at least 12 months under ambient conditions.

In specific embodiments, the oral liquid suspension, while packaged in a container, is free from microbial contamination for at least 6 months under ambient conditions.

In specific embodiments, the oral liquid suspension, while packaged in a container, is free from microbial contamination for at least 180 days under ambient conditions.

In specific embodiments, the oral liquid suspension, while packaged in a container, is free from microbial contamination for at least 90 days under ambient conditions.

In specific embodiments, the oral liquid suspension is an immediate release dosage form.

In specific embodiments, the oral liquid suspension exhibits redispersibility.

In specific embodiments, the oral liquid suspension exhibits redispersibility, such that upon turning over 3 times, the oral liquid suspension exhibits at least 80% redispersibility.

In specific embodiments, the oral liquid suspension exhibits redispersibility, such that upon turning over 3 times, the oral liquid suspension exhibits at least 85% redispersibility.

In specific embodiments, the oral liquid suspension exhibits redispersibility, such that upon turning over 3 times, the oral liquid suspension exhibits at least 90% redispersibility.

In specific embodiments, the oral liquid suspension exhibits redispersibility, such that upon turning over 3 times, the oral liquid suspension exhibits at least 95% redispersibility.

In specific embodiments, the oral liquid suspension is an immediate release dosage form that exhibits in-vitro dissolution rate more than 85% of drug release within 30 minutes, when said dosage form is placed in a dissolution vessel filled with 900 ml of 0.1N HCL, pH 1.2 maintained at 37±0.5° C. and stirred at a paddle speed of 50 rpm using a USP Type II (paddle) apparatus.

In specific embodiments, the oral liquid suspension is an immediate release dosage form that exhibits in-vitro dissolution rate more than 88% of drug release within 30 minutes, when said dosage form is placed in a dissolution vessel filled with 900 ml of 0.1N HCL, pH 1.2 maintained at 37±0.5° C. and stirred at a paddle speed of 50 rpm using a USP Type II (paddle) apparatus.

In specific embodiments, the topiramate in the oral liquid suspension has a particle size distribution $D_{90}$ of not more than 200 microns.

In specific embodiments, the topiramate in the oral liquid suspension has a particle size distribution $D_{90}$ of not more than 175 microns.

In specific embodiments, the topiramate in the oral liquid suspension has a particle size distribution $D_{90}$ of not more than 150 microns.

In specific embodiments, the topiramate in the oral liquid suspension has a particle size distribution $D_{90}$ of not more than 140 microns.

In specific embodiments, the topiramate in the oral liquid suspension has a particle size distribution $D_{50}$ of not more than 100 microns.

In specific embodiments, the topiramate in the oral liquid suspension has a particle size distribution $D_{50}$ of not more than 90 microns.

In specific embodiments, the topiramate in the oral liquid suspension has a particle size distribution $D_{50}$ of not more than 80 microns.

In specific embodiments, the topiramate in the oral liquid suspension has a particle size distribution $D_{50}$ of not more than 63 microns.

In specific embodiments, the topiramate in the oral liquid suspension has a particle size distribution $D_{10}$ of not more than 30 microns.

In specific embodiments, the topiramate in the oral liquid suspension has a particle size distribution $D_{10}$ of not more than 29 microns.

In specific embodiments, the topiramate in the oral liquid suspension has a particle size distribution $D_{10}$ of not more than 27 microns.

In specific embodiments, the topiramate in the oral liquid suspension has a particle size distribution $D_{10}$ of not more than 26 microns.

In specific embodiments, the topiramate in the oral liquid suspension has the following particle size distribution:
  $D_{90}$ of not more than 200 microns;
  $D_{50}$ of not more than 100 microns; and
  $D_{10}$ of not more than 30 microns.

In specific embodiments, the topiramate in the oral liquid suspension has the following particle size distribution:
  $D_{90}$ of not more than 139 microns;
  $D_{50}$ of not more than 64.8 microns; and
  $D_{10}$ of not more than 24.65 microns.

In specific embodiments, the topiramate employed in the manufacture of the oral liquid suspension has a particle size distribution $D_{90}$ of not more than 90 microns.

In specific embodiments, the topiramate employed in the manufacture of the oral liquid suspension has a particle size distribution $D_{90}$ of not more than 80 microns.

In specific embodiments, the topiramate employed in the manufacture of the oral liquid suspension has a particle size distribution $D_{90}$ of not more than 70 microns.

In specific embodiments, the topiramate employed in the manufacture of the oral liquid suspension has a particle size distribution $D_{50}$ of not more than 50 microns.

In specific embodiments, the topiramate employed in the manufacture of the oral liquid suspension has a particle size distribution $D_{50}$ of not more than 40 microns.

In specific embodiments, the topiramate employed in the manufacture of the oral liquid suspension has a particle size distribution $D_{50}$ of not more than 30 microns.

In specific embodiments, the topiramate employed in the manufacture of the oral liquid suspension has a particle size distribution $D_{10}$ of not more than 30 microns.

In specific embodiments, the topiramate employed in the manufacture of the oral liquid suspension has a particle size distribution $D_{10}$ of not more than 20 microns.

In specific embodiments, the topiramate employed in the manufacture of the oral liquid suspension has a particle size distribution $D_{10}$ of not more than 10 microns.

In specific embodiments, the topiramate employed in the manufacture of the oral liquid suspension has the following particle size distribution:

$D_{90}$ of not more than 70 microns;

$D_{50}$ of not more than 30 microns; and $D_{10}$ of not more than 10 microns.

In specific embodiments, the topiramate employed in the manufacture of the oral liquid suspension is amorphous.

In specific embodiments, the topiramate employed in the manufacture of the oral liquid suspension is crystalline.

In specific embodiments, the topiramate employed in the manufacture of the oral liquid suspension has a water content of not more than 1.0 wt. %.

In specific embodiments, the topiramate employed in the manufacture of the oral liquid suspension has a water content of not more than 0.75 wt. %.

In specific embodiments, the topiramate employed in the manufacture of the oral liquid suspension has a water content of not more than 0.5 wt. %.

In specific embodiments, the oral liquid suspension is administered to a subject that is a human.

In specific embodiments, the oral liquid suspension is administered to a subject human adult of at least 16 years in age (i.e., aged 16 years or older).

In specific embodiments, the oral liquid suspension is administered to a subject that is a human adult of at least 18 years in age (i.e., aged 18 years or older).

In specific embodiments, the oral liquid suspension is administered to a subject that is a human of less than 16 years in age.

In specific embodiments, the oral liquid suspension is administered to a subject that is a human aged 2 years or older (i.e., aged 2 years or older).

In specific embodiments, the oral liquid suspension is administered to treat at least one of a neurological disorder and a mental disorder in a subject.

In specific embodiments, the oral liquid suspension is administered to treat a neurological disorder in a subject.

In specific embodiments, the oral liquid suspension is administered to treat a mental disorder in a subject.

In specific embodiments, the oral liquid suspension is administered to treat at least one of a neurological disorder and a mental disorder in a subject, wherein the disorder comprises at least one of (a)-(c):
  (a) epilepsy—adjunctive therapy in a subject aged 2 years or older:
    partial-onset seizures
    primary generalized tonic-clonic seizures
    generalized seizures of Lennox-Gastaut syndrome
  (b) epilepsy—monotherapy in a subject aged 16 years and older: Conversion to monotherapy in a subject with partial-onset seizures who are receiving treatment with carbamazepine, phenytoin, phenobarbital, primidone, or valproate as the single AED
  (c) bipolar disorder: maintenance treatment of bipolar I disorder to delay the time to occurrence of mood episodes in a subject treated for acute mood episodes with standard therapy.

In specific embodiments, the disorder is epilepsy.

In specific embodiments, the oral liquid suspension is administered as an adjunctive therapy to a subject aged 2 years or older, to treat epilepsy.

In specific embodiments, the oral liquid suspension is administered as an adjunctive therapy to a subject aged 2 years or older, to treat partial-onset seizures.

In specific embodiments, the oral liquid suspension is administered as an adjunctive therapy to a subject aged 2 years or older, to treat primary generalized tonic-clonic seizures.

In specific embodiments, the oral liquid suspension is administered as an adjunctive therapy to a subject aged 2 years or older, to treat generalized seizures of Lennox-Gastaut syndrome.

In specific embodiments, the oral liquid suspension is administered as a monotherapy to a subject aged 16 years or older, to treat epilepsy.

In specific embodiments, the oral liquid suspension is administered as a monotherapy to a subject aged 16 years or older with partial-onset seizures, to treat epilepsy, wherein the subject is undergoing conversion to monotherapy and is receiving treatment with carbamazepine, phenytoin, phenobarbital, primidone, or valproate as the single AED.

In specific embodiments, the oral liquid suspension is administered to a subject to treat bipolar disorder.

In specific embodiments, the oral liquid suspension is administered to a subject for maintenance treatment of bipolar I disorder, to delay the time to occurrence of mood episodes in the subject treated for acute mood episodes with standard therapy.

In specific embodiments, the oral liquid suspension is administered, such that topiramate is administered in 25±5 mg per mL.

In specific embodiments, the oral liquid suspension is administered, such that topiramate is administered in 25±4 mg per mL.

In specific embodiments, the oral liquid suspension is administered, such that topiramate is administered in 25±3 mg per mL.

In specific embodiments, the oral liquid suspension is administered, such that topiramate is administered in 25±2.5 mg per mL.

In specific embodiments, the oral liquid suspension is administered, such that topiramate is administered in 25±1.25 mg per mL.

In specific embodiments, the oral liquid suspension is administered, such that topiramate is administered in 25 mg per mL.

In specific embodiments, the oral liquid suspension is administered, such that any one of Nos. 1-16

| No. | Volume of oral liquid suspension (mL) | Amount of topiramate (mg) |
|---|---|---|
| 1 | 0.1 | 2.5 ± 0.25 |
| 2 | 0.2 | 5 ± 0.5 |
| 3 | 0.4 | 10 ± 1.0 |
| 4 | 0.5 | 12.5 ± 1.25 |
| 5 | 0.6 | 15 ± 1.5 |
| 6 | 0.8 | 20 ± 2.0 |
| 7 | 1.0 | 25 ± 2.5 |
| 8 | 2.0 | 50 ± 5.0 |
| 9 | 2.5 | 62.5 ± 6.25 |
| 10 | 3.0 | 75 ± 7.5 |
| 11 | 4.0 | 100 ± 10.0 |
| 12 | 5.0 | 125 ± 12.5 |
| 13 | 6.0 | 150 ± 15.0 |
| 14 | 7.0 | 175 ± 17.5 |
| 15 | 8.0 | 200 ± 20.0 |
| 16 | 10.0 | 250 ± 25.0 | is delivered to the subject.

In specific embodiments, the oral liquid suspension is administered, such that any one of Nos. 1-16

| No. | Volume of oral liquid suspension (mL) | Amount of topiramate (mg) |
|---|---|---|
| 1 | 0.1 | 2.5 |
| 2 | 0.2 | 5 |
| 3 | 0.4 | 10 |
| 4 | 0.5 | 12.5 |
| 5 | 0.6 | 15 |
| 6 | 0.8 | 20 |
| 7 | 1.0 | 25 |
| 8 | 2.0 | 50 |
| 9 | 2.5 | 62.5 |
| 10 | 3.0 | 75 |
| 11 | 4.0 | 100 |
| 12 | 5.0 | 125 |
| 13 | 6.0 | 150 |
| 14 | 7.0 | 175 |
| 15 | 8.0 | 200 |
| 16 | 10.0 | 250 | is delivered to the subject.

In specific embodiments, the oral liquid suspension is administered, such 2.5±0.25 mg topiramate in 0.1 mL of the oral liquid suspension is delivered to the subject.

In specific embodiments, the oral liquid suspension is administered, such that 5.0±0.5 mg topiramate in 0.2 mL of the oral liquid suspension is delivered to the subject.

In specific embodiments, the oral liquid suspension is administered, such that 10±1.0 mg topiramate in 0.4 mL of the oral liquid suspension is delivered to the subject.

In specific embodiments, the oral liquid suspension is administered, such that 12.5±1.25 mg topiramate in 0.5 mL of the oral liquid suspension is delivered to the subject.

In specific embodiments, the oral liquid suspension is administered, such that 15±1.5 mg topiramate in 0.6 mL of the oral liquid suspension is delivered to the subject.

In specific embodiments, the oral liquid suspension is administered, such that 20±2.0 mg topiramate in 0.8 mL of the oral liquid suspension is delivered to the subject.

In specific embodiments, the oral liquid suspension is administered, such that 25±2.5 mg topiramate in 1.0 mL of the oral liquid suspension is delivered to the subject.

In specific embodiments, the oral liquid suspension is administered, such that 50±5.0 mg topiramate in 2.0 mL of the oral liquid suspension is delivered to the subject.

In specific embodiments, the oral liquid suspension is administered, such that 62.5±6.25 mg topiramate in 2.5 mL of the oral liquid suspension is delivered to the subject.

In specific embodiments, the oral liquid suspension is administered, such that 75±7.5 mg topiramate in 3.0 mL of the oral liquid suspension is delivered to the subject.

In specific embodiments, the oral liquid suspension is administered, such that 100±10 mg topiramate in 4.0 mL of the oral liquid suspension is delivered to the subject.

In specific embodiments, the oral liquid suspension is administered, such that 125±12.5 mg topiramate in 5.0 mL of the oral liquid suspension is delivered to the subject.

In specific embodiments, the oral liquid suspension is administered, such that 150±15 mg topiramate in 6.0 mL of the oral liquid suspension is delivered to the subject.

In specific embodiments, the oral liquid suspension is administered, such that 175±17.5 mg topiramate in 7.0 mL of the oral liquid suspension is delivered to the subject.

In specific embodiments, the oral liquid suspension is administered, such that 200±20 mg topiramate in 8.0 mL of the oral liquid suspension is delivered to the subject.

In specific embodiments, the oral liquid suspension is administered, such that 250±25 mg topiramate in 10.0 mL of the oral liquid suspension is delivered to the subject.

In specific embodiments, the oral liquid suspension is administered, such that
  2±0.2 mg topiramate in 0.2 mL of the oral liquid suspension, or
  5±0.5 mg topiramate in 0.5 mL of the oral liquid suspension, or
  25±2.5 mg topiramate in 2.5 mL of the oral liquid suspension, or
  100±10.0 mg topiramate in 10 mL of the oral liquid suspension, or
  150±15.0 mg topiramate in 15 mL of the oral liquid suspension, or
  200±20.0 mg topiramate in 20 mL of the oral liquid suspension
  is delivered to the subject.

In specific embodiments, the oral liquid suspension is administered, such that 2±0.2 mg topiramate in 0.2 mL of the oral liquid suspension is delivered to the subject.

In specific embodiments, the oral liquid suspension is administered, such that 5±0.5 mg topiramate in 0.5 mL of the oral liquid suspension is delivered to the subject.

In specific embodiments, the oral liquid suspension is administered, such that 25±2.5 mg topiramate in 2.5 mL of the oral liquid suspension is delivered to the subject.

In specific embodiments, the oral liquid suspension is administered, such that 100±10.0 mg topiramate in 10 mL of the oral liquid suspension is delivered to the subject.

In specific embodiments, the oral liquid suspension is administered, such that 150±15.0 mg topiramate in 15 mL of the oral liquid suspension is delivered to the subject.

In specific embodiments, the oral liquid suspension is administered, such that 200±20.0 mg topiramate in 20 mL of the oral liquid suspension is delivered to the subject.

In specific embodiments, the oral liquid suspension is administered, such that upon administration under fasted conditions of a healthy adult subject with epilepsy taking no other medications, the oral liquid suspension exhibits a pharmacokinetic (PK) profile including: AUC, 0→24 (micrograms per hour per ml) of 98-105.

In specific embodiments, the oral liquid suspension is administered, such that upon administration under fasted conditions of a healthy adult subject with epilepsy taking no other medications, the oral liquid suspension exhibits a pharmacokinetic (PK) profile including: $C_{max}$ (micrograms per ml) steady state of 1.5.

In specific embodiments, the oral liquid suspension is administered, such that upon administration under fasted conditions of a healthy adult subject with epilepsy taking no other medications, the oral liquid suspension exhibits a pharmacokinetic (PK) profile including: $T_{max}$(h) of 2-3.

In specific embodiments, the oral liquid suspension is administered, such that upon administration under fasted conditions of a healthy adult subject with epilepsy taking no other medications, the oral liquid suspension exhibits a pharmacokinetic (PK) profile including: $t_{1/2}$(h) of 19-25 (single dose).

In specific embodiments, the oral liquid suspension is administered, such that upon administration under fasted conditions of a healthy adult subject with epilepsy taking no other medications, the oral liquid suspension exhibits a pharmacokinetic (PK) profile including: $t_{1/2}$(h) of 19-25 (multiple dose).

In specific embodiments, the oral liquid suspension is administered, such that upon administration under fasted conditions of a healthy adult subject with epilepsy taking no other medications, the oral liquid suspension exhibits a pharmacokinetic (PK) profile including:

AUC, 0→24 (micrograms per ml) of 98-105;
Cmax (micrograms per ml) steady state of 1.5;
$T_{max}$(h) of 2-3;
$t_{1/2}$(h) of 19-25 (single dose); and
$t_{1/2}$(h) of 19-25 (multiple dose).

In specific embodiments, relative to oral tablets or chewable dispersible tablets containing an equivalent amount of topiramate, administration of the oral liquid suspension results in a lower incidence, severity, and/or duration of adverse reactions including at least one of dizziness, headache, diplopia, ataxia, nausea, blurred vision, somnolence, rhinitis, pharyngitis, rash, vomiting, infection, fever, accidental injury, diarrhea, abdominal pain, tremor, insomnia, somnolence, backpain, fatigue, abdominal pain, and xerostomia.

The invention will now be described with the following examples, which do not otherwise limit the scope of the invention as claimed.

EXAMPLES

Example 1

Formulation

An oral liquid suspension containing topiramate was formulated from the following substances in the amounts specified.

| % W/V (mg/ml) | Material/Component |
|---|---|
| 2.5 | topiramate |
| 0.1 | methylparaben |
| 0.03 | sodium benzoate powder |
| 0.08 | saccharin sodium dihydrate powder |
| 0.25 | sodium phosphate dibasic |
| 3 | sorbitol solution 70% |
| 2.25 | propylene glycol |
| 5 | glycerin 99% natural grade |
| 1.26 | PROSOLV® SMCC 50 (silicified microcrystalline cellulose) |
| 0.18 | carboxymethylcellulose sodium, medium viscosity (2% aqueous solution at 25° C. is 400-800 cps) |
| 0.18 | xanthan gum |
| 79.67 | purified water |
| 5 | polyethylene glycol 400 |
| 0.5 | sucralose |
| 0.2 | cherry flavor (natural and artificial) |
| 0.002 | FD&C red #40 |
| 0.0002 | FD&C yellow #6 |
| TOTAL | |
| 100.2 | |

Example 2

Method of Manufacturing

The oral liquid suspension containing topiramate of Example 1 was manufactured as follows.

Phase 1 Preparation:

1. Mix propylene glycol and methylparaben until completely dissolved and homogeneous.

Phase 2 Preparation:

1. Mix water, sodium carboxymethyl cellulose, xanthan gun!, and PROSOLV® SMCC 50M (microcrystalline cellulose and colloidal silicon dioxide) until completely dissolved and homogeneous.

2. Add sodium benzoate, sodium phosphate dibasic, and sodium saccharin and mix until completely dissolved and homogeneous.

3. Add polyethylene glycol; and mix until completely dissolved and homogeneous.

4. Add sorbitol, 70% solution and mix until completely dissolved and homogeneous.

5. Add topiramate and mix until completely dissolved and homogeneous.

Phase 3 Preparation:

1. Add Phase 1 into Phase 2 with continuous mixing, until completely dissolved and homogeneous.

2. Add glycerin and mix until completely dissolved and homogeneous.

3. Add FD&C Red #40, FD&C Yellow 46, cherry flavor, and sucralose; and mix until completely dissolved and homogeneous.

4. Semi-automatic fill in packaging (bottle) and manual labeling.

5. Optionally check appearance, pH, viscosity, particle size distribution (PSD), assay, dosage uniformity, sedimentation rate, dissolution, deliverable volume, and/or micro testing.

Example 3

Packaging

The oral liquid suspension of Example 1 was manufactured for packaging, shipment, storage, and for use with the following.

| Container | Oral Dispenser |
|---|---|
| Plastic bottle | Measuring cup |
| Glass bottle | Measuring syringe |
| | Measuring dropper |

Example 4

Method of Administration

The oral liquid suspension of Example 1 was formulated for administration that includes the following.
1. Shake well before using to ensure sufficient redispersion and content uniformity.
2. Measure the prescribed dose of the oral liquid suspension into the dispenser.
3. Orally administer the dose from the dispenser to the subject (with or without food). The medication may be administered by the patient, a caregiver, or a health professional.

Example 5

Test Methods 1.1 Appearance
 1.1.1 Procedure
Pour the suspension onto a clear and shallow glass (or plastic) dish. View over a white surface.
 1.1.2 Tolerance
Pink suspension with shades varying with concentration. The result is as reported.
1.2 Taste and Flavor
 1.2.1 Procedure
Swish about 5 mL of the suspension in the mouth for about 5 seconds.
 1.2.2 Tolerance
The suspension has a sweet cherry flavor. The result is as reported.
1.3 Water Gain or Loss
 1.3.1 Procedure
Weigh each container at the initial testing timepoint before placing into the stability chamber.
Weigh the same bottle at each stability timepoint. Record measurements until the final stability timepoint.
 1.3.2 Tolerance
As reported.
1.4 Identification A[1]
 1.4.1 Reagents

| Item | Reagent Description | Vendor/Catalog Number** |
|---|---|---|
| 1 | Ammonium Molydbate, Tetrahydrate, Crystal, Reagent, ACS | Spectrum/A1210 |
| 2 | Laboratory RO Water | In house |

**Or equivalent 1.4.2 Ammonium Molybdate Solution

Prepare a 10% (w/v) aqueous solution by dissolving 1 g of ammonium molybdate in 10 mL of water.
 1.4.3 Procedure
To 1 mL of the Assay Sample Solution (Section 1.13.6) add 1 mL of the ammonium molybdate solution and mix.
 1.4.4 Tolerance
The solution turns blue.
1.5 Identification B (USP <621>)
 1.5.1 Equipment, Reagents and Procedure
Perform the procedure described for the Assay (Section 1.13)
 1.5.2 Tolerance
The retention time of the major peak of the Sample solution corresponds to that of the Standard solution, as obtained in the Assay.
1.6 pH (USP <791>)
 1.6.1 Equipment

| ITEM | EQUIPMENT | MANUFACTURER/MODEL* | ASSET # |
|---|---|---|---|
| 1 | pH Meter | Thermo/Orion 320 | PTS 047 |
| 2 | pH Electrode | Fisherbrand/Accumet (Catalog # 13-620-289) | PTS 323 |

*Or similar calibrated/qualified equipment 1.6.2 Reagents

| ITEM | REAGENT DESCRIPTION | VENDOR/CATALOG NUMBER** |
|---|---|---|
| 1 | Buffer Solution, pH 4.00 (Certified) | Fisher Chemical/SB98-500 |
| 2 | Buffer Solution, pH 7.00 (Certified) | Fisher Chemical/SB108-500 |
| 3 | Laboratory RO Water | In house |

**Or equivalent 1.6.3 Procedure

Calibrate the pH meter using pH 4 and pH 7 buffers. Rinse the pH electrode with laboratory RO water, then with a few portions of the test sample. While gently stirring the sample on a magnetic stirrer, immerse the pH electrode into the sample and record the pH value when the measurement stabilizes. Measure in triplicate by repeating the electrode rinsing step between each measurement.
 1.6.4 Tolerance
3.9-4.9 (average, n=3).
1.7 Viscosity (USP <912>)
 1.7.1 Equipment

| ITEM | EQUIPMENT | MANUFACTURER/MODEL* | ASSET # |
|---|---|---|---|
| 1 | Rotary Viscometer | US Solid/USS DVT6 | PTS 096 |
| 2 | Spindle | US Solid/#1 or #2 sizes | N/A |

*Or similar calibrated/qualified equipment

1.7.2 Reagents

| ITEM | REAGENT DESCRIPTION | VENDOR/CATALOG NUMBER** |
|---|---|---|
| 1 | Cannon Viscosity Standards 20 mm2/s | Fisher Chemical/22-288-557 |

**Or equivalent

1.7.3 Test Conditions

| | |
|---|---|
| Temperature: | 25° C. (±0.1° C.) |
| Mode: | mPa*s |
| Spindle: | #1 or #2 |
| Spindle speed: | 60 rpm |

1.7.4 Procedure

Equilibrate the sample to 25° C. in a 150-mL beaker. Immerse the spindle to the recommended depth maintaining at least 1 cm clearance from the bottom and side of the container. Use spindle #1 or #2 depending on the depth of the available suspension, and a speed of 60 rpm. Ensure that the instrument displays a stable temperature of 25° C. (±0.1° C.). Press OK and record the viscosity when the instrument completes the measurement cycle. Perform the measurement is triplicate by pressing RESET followed by OK between measurements.

1.7.5 Tolerance

As reported (average, n=3).

1.8 Specific Gravity (USP <841>)

1.8.1 Equipment

| ITEM | EQUIPMENT | MANUFACTURER/MODEL* | ASSET # |
|---|---|---|---|
| 1 | Analytical Balance | A&D Company/GH202 | PTS 148 |

*Or similar calibrated/qualified equipment

1.8.2 Reagents

| ITEM | REAGENT DESCRIPTION | VENDOR/CATALOG NO. |
|---|---|---|
| 1 | Laboratory RO Water | In house |

**Or equivalent

1.8.3 Procedure

1. USP Method (USP <841>)

Select a scrupulously clean, dry pycnometer that previously has been calibrated by determining its weight and the weight of recently boiled water contained in it at 25° C. Adjust the temperature of the sample to about 20° C. and fill the pycnometer with it. Adjust the temperature of the filled pycnometer to 25° C., remove any excess liquid, and weigh.

2. In-House Method

Tare a clean, dry 10-mL measuring cylinder and weigh 10 mL of laboratory RO water at 25° C. Using a clean, dry 10-mL measuring cylinder weigh 10 mL of the sample at 25° C. Perform the measurements in triplicate.

1.8.4 Calculation

Subtract the tare weight of the pycnometer (or measuring cylinder) from the filled weight. The specific gravity of the liquid is the quotient obtained by dividing the weight of the sample contained in the pycnometer (or measuring cylinder) by the weight of water contained in it, both determined at 25° C.

1.8.5 Tolerance

As reported (average, n=3).

1.9 Particle Size Distribution (USP<429>)

1.9.1 Equipment

| ITEM | EQUIPMENT | MANUFACTURER/MODEL* | ASSET # |
|---|---|---|---|
| 1 | Laser Diffraction Particle Size Analyzer | Microtrac/S3500 | PTS 091 |
| 2 | Wet Sample Delivery System | Microtrac/SDC | PTS 092 |

*Or similar calibrated/qualified equipment

1.9.2 Reagents

| ITEM | REAGENT DESCRIPTION | VENDOR/CATALOG NO.** |
|---|---|---|
| 1 | Purified Water | In house |

**Or equivalent

1.9.3 Instrument Settings

| | |
|---|---|
| Dispersion Fluid: | Purified Water |
| Flow Rate: | 45% |
| Setzero Time: | 30 seconds |
| Run Time: | 30 seconds |
| Number of Runs: | 4 |
| Transparency: | Transparent |
| Particle Refractive Index: | 1.59 |
| Fluid Refractive Index: | 1.33 |
| Particle Shape: | Spherical |
| Analysis Gain: | 2 |
| Progression: | Geom 8 Root |
| Distribution: | Volume |
| Lower Edge: | 0.243 µm |
| Upper Edge: | 1408 µm |

1.9.4 Procedure

Start the flow at 45% flow rate. Select S/Z to zero the instrument. Select LOAD and ensure that the "Transmittance" is 100%. Re-disperse the suspension by shaking well and immediately add about 20 drops of the suspension into the Sample Delivery Controller (SDC) using a transfer pipette. Check the display to confirm that the particle concentration exceeds the minimum required level. Select RUN and record d10, d50 and d90 from the after each set of 4 runs.

1.9.5 Tolerance

As reported (average, n=4).

1.10 Deliverable Volume (USP <698>)

1.10.1

| ITEM | EQUIPMENT | MANUFACTURER/MODEL* | ASSET # |
|---|---|---|---|
| 1 | Digital Timer | VWR | PTS 291 |

*Or similar calibrated/qualified equipment

1.10.2 Reagent

N/A

1.10.3 Procedure

Shake the contents of 10 containers individually. Under conditions of use or as instructed in the labeling, carefully discharge the contents of each container into separate dry graduated cylinders of a rated capacity not exceeding two and a half times the volume to be measured, and calibrated "to contain". Care must be taken to avoid the formation of air bubbles during the process. In the absence of labeling instructions, support the containers at about a 30° angle to the horizontal, and gently discharge the contents into the graduated cylinder. Allow each container to drain for a period not to exceed 5 s. When free from bubbles, measure the volume of each mixture.

1.10.4 Tolerance

The average volume of liquid obtained from the 10 containers is NLT 100%, and the volume of each of the 10 containers lies within the range of 95%-110% of the volume declared in the labeling. If A, the average volume is less than 100% of that declared in the labeling, but the volume of no container is outside the range of 95%-110%, or if B, the average volume is NLT 100% and the volume of NMT 1 container is outside the range of 95%-110%, but within the range of 90%-115%, perform the test on 20 additional containers. The average volume of liquid obtained from the 30 containers is NLT 100% of the volume declared in the labeling; and the volume obtained from NMT 1 of the 30 containers is outside the range of 95%-110%, but within the range of 90%-115% of the volume declared on the labeling.

1.11 Sedimentation Rate 1.11.1 Equipment

| ITEM | EQUIPMENT | MANUFACTURER/MODEL* | ASSET # |
|---|---|---|---|
| 1 | Digital Timer | VWR | PTS 291 |

*Or similar calibrated/qualified equipment 1.11.2 Procedure

Shake the suspension well for two minutes to re-disperse. Pour 50 or 100 mL of the sample into a 100-mL measuring cylinder and start the timer. Securely seal the measuring cylinder with parafilm to prevent water loss. Measure and record the amount of sediment after 10 minutes, 1 hour, 1½ hours, 2 hours and 24 hours.

1.11.3 Tolerance

As reported.

1.12 Assessment of Re-Dispersibility 1.12.1 Procedure

Perform the procedure described in section 3.10: SEDIMENTATION RATE. After 24 hours, invert the measuring cylinder through 180°. Return to the upright position. Repeat the inversions until the suspension is uniformly distributed. Record the number of inversions required to restore uniformity.

1.12.2 Calculation

If uniformity is attained in one inversion, the suspension has 100% ease of re-dispersibility. Every additional inversion decreases the ease of re-dispersibility by 5%.

1.12.3 Tolerance

NLT 50%

1.13 Assay (<621>)

1.13.1 Equipment

| ITEM | EQUIPMENT | MANUFACTURER/MODEL* | ASSET # |
|---|---|---|---|
| 1 | HPLC System | Waters/2695 Separation Module | PTS 069 or PTS 070 |
| 2 | Detector | Waters/2410 Refractive Index Detector | PTS 072 |
| 3 | Analytical Balance | A&D Company/GH202 | PTS 148 |
| 4 | Ultrasonic Cleaner | Branson/2210R-DTH | PTS 262 |
| 5 | Wrist-Action Shaker | Burrell/Model 75 | CLL018 |

*Or similar calibrated/qualified equipment 1.13.2 Reagents and Standards

| ITEM | EQUIPMENT | VENDOR/CATALOG NUMBER** |
|---|---|---|
| 1 | Acetonitrile, HPLC Grade | Spectrum/HP419 |
| 2 | Laboratory RO Water | In house |
| 3 | USP Topiramate RS | USP/1672206 |
| 4 | USP Topiramate related compound A RS | USP/1672210 |
| 5 | USP Fructose RS | USP/1286504 |

**Or equivalent 1.13.3 Chromatographic Conditions

| | |
|---|---|
| Flow Rate: | 0.6 mL/min |
| Column: | Phenomenex Luna ® Omega 5 μm PS C18 100 Å, 250 × 4.6 mm, (Catalog Number 00G-4753-E0) or equivalent. |
| Column Temperature: | 50° C. |
| Detector Temperature: | 50° C. |
| Mobile Phase: | Acetonitrile and water (50:50) |
| Injection Volume: | 20 μL |
| Retention Time: | Approx. 7 minutes |
| Run Time: | 15 minutes |

Note: The Mobile Phase and all solutions must be prepared fresh prior to analysis.

1.13.4 Mobile Phase

Add 500 mL of acetonitrile to 500 mL of RO water and mix thoroughly. Pass the solution through a nylon filter of 0.45 μm pore size and degas by sonicating for 15 minutes.

1.13.5 Standard Solution

Accurately weigh and transfer about 50 mg of USP Topiramate RS to a 10-mL volumetric flask. Dissolve in 7 mL of Mobile Phase by shaking for 30 minutes, using a wrist-action shaker, and sonicating for 5 minutes. Allow the solution to cool to room temperature and dilute to volume with Mobile Phase. Prepare standards in duplicate (Standard A and B) and pass each standard through a fresh PTFE filter of 0.45 μm pore size.

1.13.6 Sample Solution

Re-disperse the suspension by shaking the sample bottle well. Tare a 5-mL volumetric flask. Transfer and weigh about 1 mL of the suspension into the volumetric flask. Dissolve in 3 mL of Mobile Phase by shaking for 30 minutes, using a wrist-action shaker, and sonicating for 5 minutes. Allow the solution to cool to room temperature and dilute to volume with Mobile Phase, Prepare samples in triplicate and pass each sample solution through a fresh PTFE filter of 0.45 μm pore size.

1.13.7 System Suitability Solution

Accurately weigh and transfer about 1 mg each of USP Topiramate Related Compound A RS and USP Fructose RS to a volumetric flask. Dissolve in 3 mL of Standard Solution by shaking for 30 minutes, using a wrist-action shaker, and sonicating for 5 minutes. Allow the solution to cool to room temperature and dilute to volume with Standard Solution. Pass the solution through a PTFE filter of 0.45 μm pore size.

1.13.8 Injection Format

Start with duplicate Blank injections of the Mobile Phase. Inject Standards A and B in duplicate to check the accuracy of the Standard Solution Preparation (Section 3.13.9.1). If the standard check passes, inject the System Suitability Solution in duplicate and perform six injections of Standard A (Section 3.13.9.2). If the system suitability test passes, inject samples by alternating between duplicate injections of Standard A followed by no more than four injections of the samples. The run should end with duplicate injections of Standard A.

1.13.9 Calculations 1.13.9.1 Standard Check

The accuracy of the Standard Solution Preparation should be checked by comparing the Relative Response Factor (RRF) for topiramate of each standard. The Standard Solution Preparations are not valid for the analysis unless the result of the comparison meets the specifications listed below:

$$RRF_a = \frac{Conc_a}{Resp_a}$$

$$RRF_b = \frac{Conc_b}{Resp_b}$$

$$Result = \frac{RRF_a}{RRF_b} 100$$

$$98.00 \leq Result \leq 102.00$$

Where: $Resp_a$=The absorbance response of Standard A $Resp_b$=The absorbance response of Standard B $Conc_a$=The concentration of Standard A $Conc_b$=The concentration of Standard B Result=The ratio of the response factors expressed as a percent 1.13.9.2 System Suitability Check the relative retention times for fructose, topiramate related compound A and topiramate. Check the resolution between topiramate related compound A and topiramate. Check the tailing factor and calculate the relative standard deviation of the topiramate peak area from Standard A. The HPLC system is valid if it meets the following specifications:

1. Relative retention times: Fructose (0.45), Topiramate related compound A (0.90), Topiramate (1.0).

2. Resolution: NLT 1.5 between topiramate related compound A and topiramate, System suitability solution. Tailing factor: NMT 2.0

3. Relative standard deviation: NMT 2.0%

1.13.9.3 Sample Recovery

Calculate the amount of topiramate in each sample solution as follows:

$$\text{Amount of topiramate (\%)} = \frac{Area_{spl} \times Conc_{std} \times Vol_{spl} \times 100}{Area_{std} \times Conc_{batch} \times Mass_{spl}}$$

Where:

$Area_{spl}$=Area of topiramate peak from sample solution $Area_{std}$=Area of topiramate peak in standard solution $Conc_{std}$=Theoretical standard concentration (in mg/mL)

$Conc_{batch}$=Theoretical batch concentration (in mg/mg)

$Vol_{spl}$=Sample Volume (5 mL)

$Mass_{spl}$=Sample Mass (mg)

1.13.9.4 Calculation Not

Many Chromatography systems and integrators will perform some or all of the calculations automatically. These systems should be spot checked manually to determine that they perform calculations as expected.

1.13.10 Tolerance

Topiramate oral suspension contains NLT 90.0% and NMT 110.0% of the labeled amounts of topiramate ($C_{12}H_{21}NO_8S$).

1.14 Content Uniformity (USP <905>)

1.14.1 Equipment

| ITEM | EQUIPMENT | MANUFACTURER/MODEL* | ASSET # |
|---|---|---|---|
| 1 | HPLC System | Waters/2695 Separation Module | PTS 069 or PTS 070 |
| 2 | Detector | Waters/2410 Refractive Index Detector | PTS 072 |
| 3 | Analytical Balance | A&D Company/GH202 | PTS 148 |
| 4 | Ultrasonic Cleaner | Branson/2210R-DTH | PTS 262 |
| 5 | Wrist-Action Shaker | Burrell/Model 75 | CLL018 |

*Or similar calibrated/qualified equipment 1.14.2 Reagents and Standards

| ITEM | EQUIPMENT | VENDOR/CATALOG NUMBER** |
|---|---|---|
| 1 | Acetonitrile, HPLC Grade | Spectrum/HP419 |
| 2 | Laboratory RO Water | In house |
| 3 | USP Topiramate RS | USP/1672206 |
| 4 | USP Topiramate related compound A RS | USP/1672210 |
| 5 | USP Fructose RS | USP/1286504 |

**Or equivalent

1.14.3 Chromatographic Conditions

| | |
|---|---|
| Flow Rate: | 0.6 mL/min |
| Column: | Phenomenex Luna ® Omega 5 µm PS C18 100 Å, 250 × 4.6 mm, (Catalog Number 00G-4753-E0) or equivalent. |
| Column Temperature: | 50° C. |
| Detector Temperature: | 50° C. |
| Mobile Phase: | Acetonitrile and water (50:50) |
| Injection Volume: | 20 µL |
| Retention Time: | Approx. 7 minutes |
| Run Time: | 15 minutes |

Note: The Mobile Phase and all solutions must be prepared fresh prior to analysis.

1.14.2 Mobile Phase

Add 500 mL of acetonitrile to 500 mL of RO water and mix thoroughly. Pass the solution through a nylon filter of 0.45 µm pore size and degas by sonicating for 5 minutes.

1.14.3 Standard Solution

Accurately weigh and transfer about 50 mg of USP Topiramate RS to a 10-mL volumetric flask. Dissolve in 7 mL of Mobile Phase by shaking for 30 minutes, using a wrist-action shaker, and sonicating for 5 minutes. Allow the solution to cool to room temperature and dilute to volume with Mobile Phase. Prepare standards in duplicate (Standard A and B) and pass each standard through a fresh PTFE filter of 0.45 µm pore size.

1.14.4 Sample Solution

Re-disperse the suspension by shaking the sample bottle well. Tare three 5-mL volumetric flasks. Transfer and weigh about 1 mL of the suspension from three locations, near the top, middle and bottom, respectively, of the container into each volumetric flask. Dissolve in 3 mL of Mobile Phase by shaking for 30 minutes, using a wrist action shaker, and sonicating for 5 minutes. Allow each solution to cool to room temperature and dilute to volume with Mobile Phase. Pass each sample solution through a fresh PTFE filter of 0.45 µm pore size.

1.14.5 System Suitability Solution

Accurately weigh and transfer about 1 mg each of USP Topiramate Related Compound A RS and USP Fructose RS to a 5-mL volumetric flask. Dissolve in 3 mL of Standard Solution by shaking for 30 minutes, using a wrist-action shaker, and sonicating for 5 minutes. Allow the solution to cool to room temperature and dilute to volume with Standard Solution. Pass the solution through a PTFE filter of 0.45 µm pore size.

1.14.6 Injection Format

Start with duplicate Blank injections of the Mobile Phase. Inject Standards A and B in duplicate to check the accuracy of the Standard Solution Preparation (Section 1.14.7.1). If the standard check passes, inject the System Suitability Solution in duplicate and perform six injections of Standard A (Section 1.14.7.2). If the system suitability test passes, inject samples by alternating between duplicate injections of Standard A followed by no more than four injections of the samples. The run should end with duplicate injections of Standard A.

1.14.7 Calculations

1.14.7.1 Standard Check

The accuracy of the Standard Solution Preparation should be checked by comparing the Relative Response Factor (RRF) for topiramate of each standard. The Standard Solution Preparations are not valid for the analysis unless the result of the comparison meets the specifications listed below:

$$RRF_a = \frac{Conc_a}{Resp_a}$$

$$RRF_b = \frac{Conc_b}{Resp_b}$$

$$Result = \frac{RRF_a}{RRF_b} 100$$

$$98.00 \leq Result \leq 102.00$$

Where: $Resp_a \equiv$ The absorbance response of Standard $A$
$Resp_b \equiv$ The absorbance response of Standard $B$
$Conc_a \equiv$ The concentration of Standard $A$
$Conc_b \equiv$ The concentration of Standard $B$
Result $\equiv$ The ratio of the response factors expressed as a percent 1.14.7.2 System Suitability Check the relative retention times for fructose, topiramate related compound A and topiramate. Check the resolution between topiramate related compound A and topiramate. Check the tailing factor and calculate the relative standard deviation of the topiramate peak area from Standard A. The HPLC system is valid if it meets the following specifications:
1. Relative retention times: Fructose (0.45), Topiramate related compound A (0.90), Topiramate (1.0).
2. Resolution: NLT 1.5 between topiramate related compound A and topiramate, System suitability solution. Tailing factor: NMT 2.0.
3. Relative standard deviation: NMT 2.0%.

1.14.7.3 Delivered Dose

Calculate the amount of topiramate in each sample solution as follows:

$$\text{Amount of topiramate (\%)} = \frac{\text{Area}_{spl} \times \text{Conc}_{std} \times \text{Vol}_{spl} \times 100}{\text{Area}_{std} \times \text{Conc}_{batch} \times \text{Mass}_{spl}}$$

Where:

$\text{Area}_{spl}$ = Area of topiramate peak from sample solution $\text{Area}_{std}$ = Area of topiramate peak in standard solution $\text{Conc}_{std}$ = Theoretical standard concentration (in mg/mL)

$\text{Conc}_{batch}$ = Theoretical batch concentration (in mg/mg)

$\text{Vol}_{spl}$ = Sample Volume (5 mL)

$\text{Mass}_{spl}$ = Sample Mass (mg)

Calculate the Sample standard deviation ($n = 10$) and the Acceptance Value by the formula $$|M - X| + ks$$

Where: $M$ = According to $X$, as described in Table 2 of USP <905>

$X$ = Mean of individual contents Found $k$ = Acceptability constant ($k = 2.4$, for $n = 10$)

S—sample standard deviation 1.14.7.4 Calculation Notes

Many Chromatography systems and integrators will perform some or all of the calculations automatically. These systems should be spot checked manually to determine that they perform calculations as expected.

1.14.8 Tolerance

The acceptance value of the first 10 dosage units is less than or equal to L1%. If the acceptance value is >L1%, test the next 20 units, and calculate the acceptance value. The requirements are met if the final acceptance value of the 30 dosage units is ≤L1%, and no individual content of any dosage unit is less than [1−(0.01)(L2)]M nor more than [1+(0.01)(L2)]M as specified in the Calculation of Acceptance Value under Content Uniformity in USP <905>. L1 is 15.0 and L2 is 25.0.

1.15 Chromatographic Purity (USP <621>)

1.15.1 Equipment

| ITEM | EQUIPMENT | MANUFACTURER/MODEL* | ASSET # |
|------|-----------|---------------------|---------|
| 1 | HPLC System | Waters/2695 Separation Module | PTS 069 or PTS 070 |
| 2 | Detector | Waters/2410 Refractive Index Detector | PTS 072 |
| 3 | Analytical Balance | A&D Company/GH202 | PTS 148 |
| 4 | Ultrasonic Cleaner | Branson/2210R-DTH | PTS 262 |
| 5 | Wrist-Action Shaker | Burrell/Model 75 | CLL018 |

*Or similar calibrated/qualified equipment 1.15.2 Reagents and Standards

| ITEM | EQUIPMENT | VENDOR/CATALOG NUMBER** |
|------|-----------|------------------------|
| 1 | Acetonitrile, HPLC Grade | Spectrum/HP419 |
| 2 | Laboratory RO Water | In house |
| 3 | USP Topiramate RS | USP/1672206 |
| 4 | USP Topiramate related compound A RS | USP/1672210 |
| 5 | USP Fructose RS | USP/1286504 |

**Or equivalent 1.15.3 Chromatographic Conditions

| | |
|---|---|
| Flow Rate: | 0.6 mL/min |
| Column: | Phenomenex Luna ® Omega 5 µm PS C18 100 Å, 250 × 4.6 mm, (Catalog Number 00G-4753-E0) or equivalent. |
| Column Temperature: | 50° C. |
| Detector Temperature: | 50° C. |
| Mobile Phase: | Acetonitrile and water (50:50) |
| Injection Volume: | 20 µL |
| Retention Time: | Approx. 7 minutes |
| Run Time: | 15 minutes |

Note: The Mobile Phase and all solutions must be prepared fresh prior to analysis.

3.15.4 Mobile Phase

Add 500 mL of acetonitrile to 500 mL of RO water and mix thoroughly. Pass the solution through a nylon filter of 0.45 μm pore size and degas by sonicating for 5 minutes.

1.15.5 Standard Solution

Accurately weigh and transfer about 50 mg of USP Topiramate RS to a 10-mL volumetric flask. Dissolve in 7 mL of Mobile Phase by shaking for 30 minutes, using a wrist-action shaker, and sonicating for 5 minutes. Allow the solution to cool to room temperature and dilute to volume with Mobile Phase. Prepare standards in duplicate (Standard A and B) and pass each standard through a fresh PTFE filter of 0.45 μm pore size.

1.15.6 Sample Solution

Re-disperse the suspension by shaking the sample bottle well. Transfer about 2.5 mL of the suspension into the volumetric flask. Dissolve in 1 mL of Mobile Phase by shaking for 30 minutes, using a wrist-action shaker, and sonicating for 5 minutes. Allow the solution to cool to room temperature and dilute to volume with Mobile Phase. Prepare samples in triplicate and pass each sample solution through a fresh PTFE filter of 0.45 μm pore size.

1.15.7 System Suitability Solution

Accurately weigh and transfer about 1 mg each of USP Topiramate Related Compound A RS and USP Fructose RS to a 5-mL volumetric flask. Dissolve in 3 mL of Standard Solution by shaking for 30 minutes, using a wrist-action shaker, and sonicating for 5 minutes. Allow the solution to cool to room temperature and dilute to volume with Standard Solution. Pass the solution through a PTFE filter of 0.45 μm pore size.

1.15.8 Injection Format

Start with duplicate Blank injections of the Mobile Phase. Inject Standards A and B in duplicate to check the accuracy of the Standard Solution Preparation (Section 1.15.9.1). If the standard check passes, inject the System Suitability Solution in duplicate and perform six injections of Standard A (Section 1.15.9.2). If the system suitability test passes, inject samples by alternating between duplicate injections of Standard A followed by no more than four injections of the samples. The run should end with duplicate injections of Standard A.

1.15.9 Calculations 1.15.9.1 Standard Check

The accuracy of the Standard Solution Preparation should be checked by comparing the Relative Response Factor (RRF) for topiramate of each standard. The Standard Solution Preparations are not valid for the analysis unless the result of the comparison meets the specifications listed below:

$$RRF_a = \frac{Conc_a}{Resp_a}$$

$$RRF_b = \frac{Conc_b}{Resp_b}$$

$$\text{Result} = \frac{RRF_a}{RRF_b} 100$$

$$98.00 \leq \text{Result} \leq 102.00$$

Where: $Resp_a$ ≡ The absorbance response of Standard A
$Resp_b$ ≡ The absorbance response of Standard B
$Conc_a$ ≡ The concentration of Standard A
$Conc_b$ ≡ The concentration of Standard B
Result ≡ The ratio of the response factors expressed as a percent 1.15.9.2 System Suitability Check the relative retention times for fructose, topiramate related compound A and topiramate.

Check the resolution between topiramate related compound A and topiramate. Check the tailing factor and calculate the relative standard deviation of the topiramate peak area from Standard A. The HPLC system is valid if it meets the following specifications:

1. Relative retention times: Fructose (0.45), Topiramate related compound A (0.90), Topiramate (1.0).
2. Resolution: NLT 1.5 between topiramate related compound A and topiramate, System suitability solution.
3. Tailing factor: NMT 2.0.
4. Relative standard deviation: NMT 2.0%.

1.15.9.3 Sample Recovery

Calculate the amount of topiramate in each sample solution as follows:

$$\text{Amount of topiramate (\%)} = \frac{Area_{spl} \times Conc_{std} \times Vol_{spl} \times 100}{Area_{std} \times Conc_{batch} \times Mass_{spl}}$$

Where:
$Area_{spl}$=Area of topiramate peak from sample solution
$Area_{std}$=Area of topiramate peak in standard solution
$Conc_{std}$=Theoretical standard concentration (in mg/mL)
$Conc_{batch}$=Theoretical batch concentration (in mg/mg)
$Vol_{spl}$=Sample Volume (5 mL)
$Mass_{spl}$=Sample Mass (mg)

1.15.9.4 Calculation Notes

Many Chromatography systems and integrators will perform some or all of the calculations automatically. These systems should be spot checked manually to determine that they perform calculations as expected.

1.15.10 Tolerance

Topiramate oral suspension contains NLT 90.0% and NMT 110.0% of the labeled amounts of topiramate ($C_{12}H_{21}NO_8S$).

1.16 Related Compounds (USP <621>)

1.16.1 Equipment

| ITEM | EQUIPMENT | MANUFACTURER/MODEL* | ASSET # |
|------|-----------|---------------------|---------|
| 1 | HPLC System | Waters/2695 Separation Module | PTS 069 or PTS 070 |
| 2 | Detector | Waters/2410 Refractive Index Detector | PTS 072 |
| 3 | Analytical Balance | A&D Company/GH202 | PTS 148 |
| 4 | Ultrasonic Cleaner | Branson/2210R-DTH | PTS 262 |
| 5 | Wrist-Action Shaker | Burrell/Model 75 | CLL018 |

*Or similar calibrated/qualified equipment

1.16.2 Reagents and Standards

| ITEM | EQUIPMENT | VENDOR/CATALOG NUMBER** |
|------|-----------|--------------------------|
| 1 | Acetonitrile, HPLC Grade | Spectrum/HP419 |
| 2 | Laboratory RO Water | In house |
| 3 | USP Topiramate RS | USP/1672206 |
| 4 | USP Topiramate related compound A RS | USP/1672210 |

**Or equivalent

1.16.3 Chromatographic Conditions

| | |
|---|---|
| Flow Rate: | 0.6 mL/min |
| Column: | Phenomenex Luna ® Omega 5 μm PS C18 100 Å, 250 × 4.6 mm, (Catalog Number 00G-4753-E0) or equivalent. |
| Column Temperature: | 50° C. |
| Detector Temperature: | 50° C. |
| Mobile Phase: | Acetonitrile and water (50:50) |
| Injection Volume: | 50 μL |
| Retention Time: | Approx. 7 minutes |
| Run Time: | 40 minutes (or NLT 5 times the retention time of topiramate) |

Note: The Mobile Phase and all solutions must be prepared fresh prior to analysis.

1.16.4 Mobile Phase

Add 500 mL of acetonitrile to 500 mL of RO water and mix thoroughly. Pass the solution through a nylon filter of 0.45 μm pore size.

1.16.5 Standard Solution

Accurately weigh and transfer about 12 mg of USP Topiramate RS and 6 mg of USP Topiramate Related Compound A RS to a 10-mL volumetric flask. Dissolve in 7 mL of Mobile Phase by shaking for 30 minutes, using a wrist action shaker, and sonicating for 5 minutes. Allow the solution to cool to room temperature and dilute to volume with Mobile Phase. Pass the standard solution through a fresh PTFE filter of 0.45 μm pore size.

1.16.6 Peak Identification Solution

Accurately weigh and transfer about 6 mg of USP Topiramate RS and 6 mg of USP Topiramate Related Compound A RS to a 10-mL volumetric flask. Dissolve in 7 mL of Mobile Phase by shaking for 30 minutes, using a wrist action shaker, and sonicating for 5 minutes. Allow the solution to cool to room temperature and dilute to volume with Mobile Phase. Pass the standard solution through a fresh PTFE filter of 0.45 μm pore size.

1.16.7 Sample Solution

Re-disperse the suspension by shaking the sample bottle well. Tare a 5-mL volumetric flask. Transfer and weigh about 1 mL of the suspension into the volumetric flask. Dissolve in 3 mL of Mobile Phase by shaking for 30 minutes, using a wrist-action shaker, and sonicating for 5 minutes. Allow the solution to cool to room temperature and dilute to volume with Mobile Phase. Pass each sample solution through a fresh PTFE filter of 0.45 μm pore size.

1.16.8 Injection Format

Start with duplicate Blank injections of the Mobile Phase. Inject the Peak Identification Solution in duplicate and perform six injections of the Standard Solution (Section 1.16.9.1). If the system suitability test passes, inject samples by alternating between duplicate injections of the Standard Solution followed by no more than four injections of the samples. The run should end with duplicate injections of the Standard Solution.

1.16.9 Calculations

1.16.9.1 System Suitability

Identify the peaks due to topiramate related compound A and topiramate using the relative retention times. Calculate the relative standard deviation and of the topiramate peak area from Standard A. The HPLC system is valid if it meets the following specifications:

1. Relative retention times: Topiramate related compound A (0.66), Topiramate (1.0)
2. Relative standard deviation: NMT 5.0%

1.16.9.2 Sample Recovery

Calculate the percentage of each impurity in the portion of Suspension taken:

$$\text{Result} = (r_U/r_S) \times (C_S/C_U) \times (1/F) \times 100$$

Where:

$r_U$=peak response for the individual impurity from the Sample solution $r_S$=peak response of topiramate from the Standard solution $C_S$=concentration of USP Topiramate RS in the Standard solution (mg/mL)

$C_U$=nominal concentration of topiramate in the Sample solution (mg/mL)

F=relative response factor

1.16.9.3 Calculation Notes

Many Chromatography systems and integrators will perform some or all of the calculations automatically. These systems should be spot checked manually to determine that they perform calculations as expected.

1.16.10 Tolerance

Topiramate related compound A: NMT 0.5%
Individual unspecified degradation product: NMT 0.2%
Total impurities: NMT 0.7%

1.17 Dissolution (USP <711>)

1.17.1 Equipment

| ITEM | EQUIPMENT | MANUFACTURER/MODEL* | ASSET # |
|------|-----------|---------------------|---------|
| 1 | HPLC System | Waters/2695 Separation Module | PTS 069 or PTS 070 |
| 2 | Detector | Waters/2410 Refractive Index Detector | PTS 072 |
| 3 | Analytical Balance | A&D Company/GH202 | PTS 148 |
| 4 | Ultrasonic Cleaner | Branson/2210R-DTH | PTS 262 |
| 5 | Wrist-Action Shaker | Burrell/Model 75 | CLL018 |

*Or similar calibrated/qualified equipment

1.17.2 Reagents and Standards

| ITEM | EQUIPMENT | VENDOR/CATALOG NUMBER** |
|------|-----------|-------------------------|
| 1 | Acetonitrile, HPLC Grade | Spectrum/HP419 |
| 2 | Laboratory RO Water | In house |
| 3 | USP Topiramate RS | USP/1672206 |

**Or equivalent

1.17.3 Dissolution Conditions

| | |
|---|---|
| Apparatus: | Apparatus 2 (Paddles) |
| Dissolution Medium: | Purified Water (degassed) |
| Volume: | 900 mL |
| Revolutions per minute: | 50 rpm |
| Temperature: | 37° C. + 0.5° C. |
| Cannula Tip Filters: | Hanson 45 μm (QLA LLC. Catalog number FIL045-HR-1000) |
| Sampling times: | 5, 10, 20, 30 and 40 minutes |
| Minimum number of units to test: | 6 units (12 units for clinical testing product) |
| Sample Volume: | 10 mL at each time point |

1.17.4 Chromatographic Conditions

| | |
|---|---|
| Flow Rate: | 1.0 mL/min |
| Column: | Phenomenex Luna ® Omega 5 μm PS C18 100 Å, 250 × 4.6 mm, (Catalog Number 00G-4753-E0) or equivalent. |
| Column Temperature: | 30° C. |
| Detector Temperature: | 50° C. |
| Mobile Phase: | Acetonitrile and water (1:1) |
| Injection Volume: | 100 μL |
| Retention Time: | Approx. 8 minutes |
| Run Time: | 15 minutes |

1.17.5 Dissolution Medium

Warm purified water to about 40° C., degas and dispense 900 mL of medium directly into each dissolution vessels. Equilibrate the media to the bath temperature. Measure and record media temperatures in each vessel immediately before adding the sample.

1.17.6 Mobile Phase

Mix 500 mL of RO water and 500 mL of acetonitrile in a 1000-mL beaker. Mix well and filter through a 0.45 μm nylon filter and degas by sonicating for 15 minutes.

1.17.7 Standard Solution Preparation

Accurately weigh and transfer about 10 mg of USP Topiramate RS, to a 100-mL volumetric flask. Dissolve in 70 mL of Dissolution Medium by shaking for 30 minutes, using a wrist action shaker, and sonicating for 5 minutes. Allow the solution to cool to room temperature and dilute to volume with Dissolution Medium. Prepare in duplicate to make Standard A and Standard B. Filter each sample using a fresh 0.45 μm filter before HPLC analysis.

1.17.8 Sample Preparation

Shake the Topiramate suspension thoroughly. Accurately weigh about 4 mL of the suspension in 5-mL luer-lock syringes and carefully transfer the entire volume into the center-bottom of each dissolution vessel. Avoid agitating the suspension during transfer. Start the dissolution run immediately after all samples have been loaded. At the specified sampling time, manually sample 10 mL of dissolution media through 45 μm cannula-tip filters. Pass each sample through fresh PTFE filters of 0.45 μm pore size before HPLC analysis.

1.17.9 Injection Format

Start with duplicate injections of Dissolution Media. Perform duplicate injections of Standard A and Standard B to check standard preparation (Section 1.17.10.1). If the standard check passes, proceed with at least six injections of Standard A to determine system suitability (Section 1.17.10.2). If the system suitability test passes, test the samples by alternating between two injections of Standard A followed by no more than twelve injections of the samples. The run should end with duplicate injections of Standard A.

1.17.10 Calculations

1.17.10.1 Standard Check

The accuracy of the Standard Solution should be checked by comparing the Relative Response Factor (RRF) for Topiramate of each standard. The Standard Solution are not valid for the analysis unless the result of the comparison meets the specifications listed below:

$$RRF_a = \frac{Conc_a}{Resp_a}$$

$$RRF_b = \frac{Conc_b}{Resp_b}$$

$$Result = \frac{RRF_a}{RRF_b} 100$$

$$98.00 \leq Result \leq 102.00$$

Where: $Resp_a$ ≡ The absorbance response of Standard A
$Resp_b$ ≡ The absorbance response of Standard B
$Conc_a$ ≡ The concentration of Standard A
$Conc_b$ ≡ The concentration of Standard B
Result ≡ The ratio of the response factors expressed as a percent

1.17.10.2 System Suitability Check

Calculate relative standard deviation of topiramate peak area for six injections of the Standard Solution. The HPLC system is valid if it meets the following specifications:
1. Column Efficiency: NLT 5000 theoretical plates
2. Tailing Factor: NMT 2.0
3. % RSD: NMT 2.0%
4. Where % RSD=Relative Standard Deviation of Standard Solution peak Area

1.17.10.3 Percent Dissolved

Calculate the amount of Topiramate recovered at each sample time point. Calculate the average, the standard deviation and the relative standard deviation. The found value for each sample should be calculated as follows:

$$RRF = \frac{Conc_{std}}{Area_{std}}$$

$$Conc_{spl} = Area_{spl} RRF$$

$$removed_{sampl.} = Conc_{spl} Volume_{spl}$$

$$Found = 100((Conc_{spl} Scalar) + removed_{prev})/Label$$

Where: Found = Amount dissolved found in sample expressed as a percent $Conc_{spl}$ = Found concentration of the sample in mg/mL $Area_{spl}$ = Area found for the sample $Area_{std}$ = Area found for the standard $Conc_{std}$ = Theoretical concentration of the standard in mg/mL RRF = Relative response factor of the standard $Removed_{spl}$ = The amount of material removed during sampling (mg)

$Removed_{prev}$ = The sum of $Removed_{spl}$ from all previous sample times (mg)

Scalar = see Scalar Table

Label = The labeled strength of the sample in mg

Scalar Table

| Sample Point (minutes) | Scalar |
|---|---|
| 5 | 900 |
| 10 | 890 |
| 20 | 880 |
| 30 | 870 |
| 40 | 860 |

1.17.10.4 Calculation Notes

Many HPLC systems and data systems will perform some or all of the calculations automatically. These systems should be spot checked manually to determine that they perform calculations as expected.

3.17.11 Tolerance

NLT 80% of the labeled amount (Q) of topiramate (C12H21NO8S) is dissolved in 40 minutes (average, n=6 or 12). Report % RSD.

1.18 Microbial Testing (USP <61>)

1.18.1 Equipment

| ITEM | EQUIPMENT | Manufacturer/Model* | Asset Number |
|---|---|---|---|
| 1 | CO₂ Incubator | Sanyo/MCO20AIC | LIF-0001 |
| 2 | CO₂ Incubator | Sanyo/MCO20AIC | LIF-0049 |

*Or similar calibrated/qualified equipment

1.18.2 Reagents and Standards

| ITEM | Reagents and Materials | VENDOR/CATALOG NUMBER** |
|---|---|---|
| 1 | Heterotrophic Plate Count Sampler (HPC, Red) | Millipore/MHPC10025 |
| 2 | Yeast and Mold Sampler (YM, Yellow) | Millipore/MHPC10025 |

**Or equivalent

1.18.3 Challenge Organisms for Positive Controls

| | ATCC Number |
|---|---|
| Aerobic bacteria | |
| *Staphylococcus aureus* | ATCC 6538 |
| *Bacillus spizizenii* | ATCC 6633 |
| *Pseudomonas aeruginosa* | ATCC 9027 |
| Anaerobic bacterium | |
| *Clostridium sporogenes* | ATCC 19404 |
| Fungi | |
| *Candida albicans* | ATCC 10231 |
| *Aspergillus brasiliensis* | ATCC 16404 |

1.18.4 Procedure

Note: This procedure should be completed under sterile laboratory conditions.

Disinfect the outer package of each test article, HPC and YM samplers prior to testing using a sterile clean room wipe moistened with a germicidal. Write on the Sampler case with indelible marker the date and sample identification information. Open the Sampler package, lift out the sampler and carefully remove the paddle from its case. Pour the Sample liquid into the sample case, filling the upper (18 mL) graduation. Insert the Sampler firmly into the case containing sample, and carefully lay the unit with the membrane facing down onto a flat surface. Make sure the membrane is uniformly wetted, and while in this position, the unit should not be agitated. Allow 30 seconds for sample to be drawn through the filter and ensure there are no more bubbles coming out of the vent prior to removing the paddle from the sample. Remove the paddle and, with a firm snap of the wrist, shake off the excess liquid. Empty the case and re-insert the paddle. Ensure that the paddle is seated firmly in the case to form an airtight seal.

Incubate the HPC Sampler at 30-35° C. for 48-72 hours and the YM Sampler 20-25° C. for 24-72 hours, with the gridded side facing down. Examine both samplers after an initial 24 hours (and thereafter, every 24 hours) and obtain images of both the sample information on the sampler case and the gridded side of the sampler.

1.18.5 Negative Controls

Incubate fresh HPC Sampler at 30-35° C. for 48-72 hours and the YM Sampler 20-25° C. for 24-72 hours, with the gridded side facing down. Examine both samplers after an initial 24 hours (and thereafter, every 24 hours) and obtain images of both the sample information on the sampler case and the gridded side of the sampler.

1.18.6 Preparation of Positive Controls

Prepare the following:

Handling bacteria requires full gowning, head and toe, the use of sterile gloves only and work in the hood. The hood requires full cleaning with peroxide and alcohol. Take some contact plates before, and sedimentation plates during processing. Full gowning, with face and hands control, followed by cleaning well after the work are important.

Growth promotion test with EZ-Accu Shot™ microorganisms:

1. INTENDED USE of EZ-Accushot:

EZ-Accu Shot™ Microorganisms are lyophilized, quantitative microorganism preparations to be used for Quality Control purposes. Processed as directed, these preparations provide a challenge of <100 CFU per 0.1 mL. This is the required concentration for growth promotion testing of culture media to be employed in most microbial enumeration tests, tests for specified microorganisms, and sterility tests. These microorganism preparations are traceable to the American Type Culture Collection (ATCC®) or other authentic reference culture collections. (Record lot number, ATCC numbers and how prepared)

2. SPECIFICATIONS AND PERFORMANCE:

EZ-Accu Shot™ Microorganisms are packaged in a kit configuration. Each kit consists of:

Five (5) vials each containing one (1) lyophilized pellet of an individual microorganism strain Five (5) Hydrating Fluid vials each containing 1.2 mL of hydrating fluid Detailed instructions Certificate of Assay 3. Processed as directed, EZ-Accu Shot™ Microorganisms will provide a challenge concentration of <100 CFU per 0.1 mL. Quality control documentation includes, but is not limited to, a Certificate of Assay stating:

The identity of the microorganism

The traceability of the microorganism to a reference culture

That the microorganism preparation has been removed not more than four (4) passages from the reference culture The mean assay value for the microorganism preparation Precautions and Limitations These products are for in-vitro use only. These devices, and subsequent growth of these microorganisms on culture media, are considered to be biohazard material. These devices contain viable microorganisms that may, under certain circumstances, produce disease. Proper techniques must be employed to avoid exposure and contact with any microorganism growth.

The microbiology laboratory must be equipped, and have the facilities to receive, process, maintain, store and dispose of biohazard, material.

Microbiology laboratory personnel using these devices must be educated, experienced and demonstrate proficiency in processing, maintaining, storing and disposing of biohazard material.

Agencies and statutes do regulate the disposal of all biohazard materials. Each laboratory must be aware of, and comply with, the proper disposal of biohazard materials A. Material Preparation All the materials required for the challenge procedure and the materials to be challenged must be ready for use immediately following the hydration step. Following the hydration of the lyophilized strain, challenge inoculation(s) MUST be completed within 8 hours. The remaining suspension must be refrigerated at 2-8° C. between use to avoid a change in the challenge suspension concentration.

B. Hydration

1. Remove the Hydrating Fluid vial and vial containing lyophilized strain preparation (pellet) from refrigerated storage. Allow the lyophilized strain preparation and the Hydrating Fluid to equilibrate to room temperature.
2. Transfer ONE (1) pellet into the 1.2 mL vial of Hydrating Fluid under aseptic condition
3. ONLY ONE PELLET MUST BE USED TO OBTAIN THE CHALLENGE CONCENTRATION OF <100 CFU per 0.1 mL.
4. Immediately recap the vial with the hydrated material.
5. Vortex the hydrated material to achieve a homogeneous suspension.
6. Refrigerate suspension at 2-8° C. if not used right away.

C. Inoculation

1. Under aseptic condition, use a 1 mL syringe (graduated every 0.1 mL) equipped with a sterile needle.
2. Inject 0.1 mL of the inoculum into each medium to be challenged.
3. Proceed with the challenge procedure according to laboratory protocol.
4. Refrigerate suspension in the syringe at 2-8° C. if it will be used again.
5. Discard any remaining hydrated material in accordance with the laboratory protocol for disposal of biohazard materials.

Fill each sampler to the 18 mL mark with sterile water for injection. Inoculate the HPC Sampler with *S. aureus, P. aeruginosa, B. subtilis,* and *C. sporogene* and incubate at 30-35° C. for at least 48 hours.

Inoculate the YMSampler with *C. albicans,* and *A. brasiliensis* and incubated at 20-25° C. for 4 days.

1.18.7 Sampler Examination

For the HPC Samplers, colonies appear glistening and translucent or transparent. Colors vary from colorless to white, cream yellow or occasionally pigmented. Magnification of colonies is recommended for counting colonies. Mold colonies appear white, green or brown/black and filamentous. Bacterial colonies may appear but are usually smaller and more glistening and transparent than the yeast colonies.

1.18.8 Tolerance

The sample should meet the following specifications:

| Total Aerobic Microbial Count (TAMC) | ≤100 cfu/mL |
|---|---|
| Combined Yeasts and Molds (TYMC) | ≤10 cfu/mL |

Example 6

Storage Stability Test

The storage stability of the suspension has been tested over a 6-month storage period under accelerated conditions 40° C. and 75% RH for a period of 6 months and for 24 months at 25° C. and 60% RH. Sufficient bottles of 236 mL bottles were stored at these conditions at each time point of the stability program the composition of suspension was analyzed by HPLC chromatography and the amount of topiramate and its known impurities were determined by a validated HPLC assay. Other tests such as sedimentation rate or redispersibility, during the storage period.

Example 7

Pharmacokinetics (PK)

Pharmacokinetics (PK) of topiramate were obtained after administration of a single dose of oral liquid suspension in a human volunteer, using the following protocols.

Synopsis of PK Studies 1.0 Protocol Summary—Pilot Study—Fasting Condition

| | |
|---|---|
| Study Title | An open-label, randomized, balanced, single-dose, two-treatment, two-period, two-sequence, cross-over, oral bioavailability study of Topiramate oral suspension 25 mg/mL Manufactured by OWP Pharmaceuticals, Inc, 400 East Diehl Road, Suite 400, Naperville, IL 60563 with TOPAMAX ® (topiramate) tablets, 100 mg manufactured by Janssen Ortho LLC Gurabo, Puerto Rico 00778 and manufactured for Janssen Pharmaceuticals, Inc. Titusville, NJ 08560 in healthy, adult, human, male subjects under fasting conditions. |
| Study Objectives | 1. To compare the oral bioavailability of Topiramate oral suspension 25 mg/mL of OWP Pharmaceuticals, Inc, 400 East Diehl Road, Suite 400, Naperville, IL 60563 with TOPAMAX ® (Topiramate) tablets, 100 mg manufactured by Janssen Ortho LLC Gurabo, Puerto Rico 00778 and manufactured for Janssen Pharmaceuticals, Inc. Titusville, NJ 08560 in healthy, adult, human, male subjects under fasting conditions.<br>2. To evaluate subject safety and tolerability of investigational products. |
| Study Design | An open-label, randomized, balanced, single-dose, two-treatment, two-period, two-sequence, cross-over, oral bioequivalence study in 18 healthy, adult, human, male subjects under fasting conditions. |
| Number of Subjects | Eighteen (18) healthy, adult, human, male subjects will be enrolled into the study.<br>One additional subject will be enrolled to compensate for any withdrawn/dropout prior to the dosing of Period-I. If any subject withdraws/drops out due to any reason prior to the dosing in Period-I, he will be replaced with the additional enrolled subject to ensure the dosing of 18 subjects as per in-house SOP. |
| Investigational Drug Products | Test (T)  Topiramate oral suspension 25 mg/mL Manufactured by: OWP Pharmaceuticals, Inc, 400 East Diehl Road, Suite 400, Naperville, IL 60563<br>Reference (R)  TOPAMAX ® (Topiramate) tablets, 100 mg Manufactured by: Janssen Ortho, LLC Gurabo, Puerto Rico 00778. Manufactured for: Janssen Pharmaceuticals, Inc. Titusville, NJ 08560. |
| Drug Administration | Subjects should comply at least 10.00 hours overnight fasting prior to drug administration and no food will be allowed at least 4.00 hours post dose in each period.<br>As per the randomization schedule, subject will receive Test or reference product in each period. Subjects will receive Test product once and Reference product once by end of the study.<br>The clock time when each dose is administered will be recorded on the Case Report Forms.<br>Reference Product Administration: |
| | One tablet of reference product [Topamax ® (Topiramate) tablets 100 mg] will be administrated to the subject with 240 ± 02 mL of drinking water at room temperature in sitting posture, under fasting conditions.<br>Subjects will be instructed do not chew, crash, or break the tablet and swallow whole.<br>The clinical staff will ensure that the study participant has swallowed the medication by performing mouth check using torchlight and Spatula/tongue depressor.<br>Test product Administration: |
| | 4 mL of test product (topiramate oral suspension 25 mg/mL) will be slowly administered orally, directly into the corner of the mouth until the liquid medicine in the syringe is completed, to the subjects |

| | |
|---|---|
| | using a disposable graded syringe at room temperature in sitting posture, under fasting conditions.<br>After subjects swallow oral suspension, the drag-dispensing container (syringe) will be rinsed with an adequate amount of water until it is free of medicine and allowed to swallow the rinse. The remaining amount of water from 240 ± 02 mL will be administered at room temperature in sitting posture, under fasting condition. Subjects will be instructed do not spit the suspension and swallow entirely (as a whole dosage). |
| Admission and Stay | Study participants will be housed in the Clinical Pharmacology Unit (CPU) from at least 11.00 hours before drug administration to 48.00 hours after drug administration. |

Sample Management

| | |
|---|---|
| Sampling Time Points | In each period, total 22 (1 × 4 mL) blood samples will be collected as per the following schedule:<br>Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50, 4.00, 6.00, 8.00, 10.00, 12.00, 16.00, 24.00, 36.00, 48.00 and 72.00 hours into 4 ml K$_2$EDTAvacutainers. |

| | In-house | Ambulatory | Total |
|---|---|---|---|
| | 21 | 01 | 22 |

| | | | |
|---|---|---|---|
| Blood Loss | Screening | | Up to 12 mL |
| | Study | | 176 mL |
| | Discarding the Saline mixed blood | | Up to 17 mL |
| | Post Study | | Up to 12 mL |
| | Total | | Approximately 217 mL. |
| Anticoagulant | K$_2$EDTA | | |
| Centrifugation Details | 3800 RPM for 10 minutes at 4° C. ± 2° C. | | |
| Sample Storage Conditions | Samples will be stored at −70° C. ± 15° C. until drawn for analysis. | | |
| No. of Aliquots | Two | | |
| Analytical Methods | The plasma concentration of Topiramate will be quantified in plasma using validated analytical method. | | |
| Pharmacokinetic Parameters | Primary Parameters: C$_{max}$ AUC$_{0-t}$ and AUC$_{0-inf}$<br>Secondary Parameters: T$_{max}$, K$_{el}$ and t$_{1/2}$. | | |
| Bioequivalence Criteria | Based on the Analysis, Bioequivalence is declared if the Test products (T) and Reference (R) ratios of the geometric least squares means for ln-transformed pharmacokinetic parameters C$_{max}$, AUC$_{0-t}$ and AUC$_{0-inf}$ and their 90% confidence intervals are within 80.00%-125.00% for Topiramate. | | |
| Ethical Issues | The study will commence only after a written approval is obtained from the Ethics Committee (EC). The study will be conducted as per New Drugs and Clinical Trials Rules 2019 G.S.R 227(E) dated: 19 Mar. 2019; Ethical Guidelines for Biomedical Research on Human Participants, Good Clinical Laboratory Practice (GCLP), ICMR (Indian Council of Medical Research; 2017), Declaration of Helsinki (64th WMA General Assembly, Fortaleza, Brazil, October 2013), ICH E6 R2 (Step 5) 'Guidance on Good Clinical Practice', Guidance for Industry Bioavailability and Bioequivalence Studies for Orally Administered Drug Products - General Considerations - U. S. Department of Health and Human Service Food and Drug Administration, Center for Drug Evaluation and Research (CDER) March 2003; 21 CFR (Code of Federal Regulations) and all other applicable regulatory requirements. | | |

2.0 Protocol Summary—Pilot Study—Food Effect

| | |
|---|---|
| Study Title | An open-label, balanced, randomized, single-dose, two-treatment, three-period, six-sequence, cross-over, oral food effect and fed comparative bioavailability and bioequivalence study of Topiramate oral suspension 25 mg/mL of OWP Pharmaceuticals, Inc, 400 East Diehl Road, Suite 400, Naperville, IL 60563, with TOPAMAX ® (Topiramate) tablets, 100 mg manufactured by Janssen Ortho LLC Gurabo, Puerto Rico 00778 and manufactured for Janssen Pharmaceuticals, Inc. Titusville, NJ 08560 in healthy, adult, human, male subjects. |
| Study Objectives | 1.     To compare the rate and extent of absorption of Topiramate Oral Suspension 25 mg/mL of OWP Pharmaceuticals, Inc, 400 East Diehl Road, Suite 400, Naperville, IL 60563 with |

| | | |
|---|---|---|
| | | TOPAMAX ® (Topiramate) tablets 100 mg manufactured by Janssen Ortho LLC Gurabo, Puerto Rico 00778 and manufactured for Janssen Pharmaceuticals, Inc. Titusville, NJ 08560 in healthy, adult, human, male subjects under fed condition. |
| | 2. | To evaluate the effect of food on the rate and extent of absorption of Topiramate Oral Suspension 25 mg/mL of OWP Pharmaceuticals, Inc, 400 East Diehl Road, Suite 400, Naperville, IL 60563 in healthy, adult, human, male subjects. |
| | 3. | To evaluate the subject safety and tolerability of investigational products. |
| Study Design | An open label, balanced, randomized, single-dose, two-treatment, three-period, six-sequence, cross-over, oral food effect and fed comparative bioequivalence study in 36 healthy adult human male subjects. | |
| Number of Subjects | Thirty-Six (36) healthy, adult, human male subjects will be enrolled into the study. Two additional subjects will be enrolled to compensate for any withdrawn/dropout prior to the dosing of Period-I. If any subject withdraws/drops out due to any reason prior to the dosing in Period-I, he will be replaced with the additional enrolled subject to ensure the dosing of 36 subjects as per in-house SOP. | |
| Investigational Drug Products | Test (T) | Topiramate oral suspension 25 mg/mL Manufactured by: OWP Pharmaceuticals, Inc, 400 East Diehl Road, Suite 400, Naperville, IL 60563 |
| | Reference (R) | TOPAMAX ® (Topiramate) tablets, 100 mg Manufactured by: Janssen Ortho, LLC Gurabo, Puerto Rico 00778 Manufactured for: Janssen Pharmaceuticals, Inc. Titusville, NJ 08560 |
| Washout Period | At least 21 days, between each drug administration | |
| Duration of the study | The minimum duration of this study will be at least 47 days (including a gap of washout period of 21 days between each periods of the study). | |
| Drug Administration | As per the randomization schedule, each subject will receive Test product (T) twice and Reference product (R) once as per randomization cross-over design by end of the study The clock time when each dose is administered will be recorded on the Case Report Forms. Test Treatment Fasting conditions: After an overnight fasting of at least 10.00 hours prior to administration. Test Treatment Fed condition: After an overnight fasting of at least 10.00 hours, a high fat and high calorie breakfast will be served 30 minutes prior to administration. Reference Treatment Fed condition: After an overnight fasting of at least 10.00 hours, a high fat high calorie breakfast will be served 30 minutes prior to administration. Test Treatment Fasting conditions: 4 mL of test product (topiramate oral suspension 25 mg/mL) will be slowly administered orally, directly into the corner of the mouth until the liquid medicine in the syringe is completed, to the subjects using a disposable graded syringe at room temperature in sitting posture, under fasting conditions. After subjects swallow oral suspension, the drug-dispensing container (syringe) will be rinsed with an adequate amount of water until it is free of medicine and allowed to swallow the rinse. The remaining amount of water from 240 ± 02 mL will be administered at room temperature in sitting posture, under fasting condition. Subjects will be instructed do not spit the suspension and swallow entirely (as a whole dosage). Test Treatment Fed condition: 4 mL of test product (Topiramate oral suspension 25 mg/mL) will be slowly administered orally, directly into the corner of the mouth until the liquid medicine in the syringe is completed, to the subjects using a disposable graded syringe at room temperature in sitting posture, under fed conditions. After subjects swallow oral suspension, the drug-dispensing container (syringe) will be rinsed with an adequate amount of water until it is free of medicine and allowed to swallow the rinse. The remaining amount of water from 240 ± 02 mL will be administered at room temperature in sitting posture. Subjects will be instructed do not spit the suspension and swallow whole. Reference Treatment Fed condition: One tablet of reference product (TOPAMAX ® (Topiramate) tablets, 100 mg) will be administered to the subjects in sitting posture with 240 ± 02 mL water, under fed conditions. Subjects will be instructed do not chew or crush the tablet and swallow whole. | |

| | -continued | | |
|---|---|---|---|
| Admission and Stay | The clinical staff will ensure that the study participant has swallowed the medication by performing mouth check using torchlight and Spatula/tongue depressor.<br>Study participants will be housed in the Clinical Pharmacology Unit (CPU) from at least 11.00 hours before drug administration to 48.00 hours after drug administration. | | |
| | Sample Management | | |
| Sampling Time Points | In each period, total 22 (1 × 4 mL) blood samples will be collected as per the following schedule:<br>Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50, 4.00, 6.00, 8.00, 10.00, 12.00, 16.00, 24.00, 36.00, 48.00 and 72.00 hours into 4 ml K2EDTAvacutainers. | | |
| | In-house | Ambulatory | Total |
| | 21 | 01 | 22 |
| Blood Loss | Screening<br>Study<br>Discarding the Saline mixed blood<br>Post Study | | Up to 12 mL<br>264 mL<br>Up to 26 mL<br>Up to 12 mL |
| | Total | | Approximately 314 mL |
| Anticoagulant | $K_2$EDTA | | |
| Centrifugation Details | 3800 RPM for 10 minutes at 4° C. ± 2° C. | | |
| Sample Storage Conditions | Plasma samples will be stored at −70° C. ± 15° C. until drawn for bioanalysis. | | |
| No. of Aliquots | Two | | |
| Analytical Methods | The plasma concentrations of Topiramate will be quantified in plasma using validated analytical method. | | |
| Pharmacokinetic Parameters | Primary Parameters: $C_{max}$ $AUC_{0-t}$ and $AUC_{0-inf}$<br>Secondary Parameters: $T_{max}$, $K_{el}$ and $t_{1/2}$. | | |
| Criteria for Evaluation | Based on the statistical results of 90% confidence interval for the ratio of the geometric least squares mean for log-transformed pharmacokinetic parameters $C_{max}$, $AUC_{0-t}$, and $AUC_{0-inf}$ for Topiramate conclusion will be drawn for Test (fed) versus Reference (fed) and Test (fasting) versus Test (fed) treatment.<br>Absence of food effect on bioavailability of test product will be established if the 90 percent confidence intervals for the ratio of population geometric means between Test (fasting) and Test (fed) treatments, based on log-transformed data, are contained in the equivalence limits of 80.00-125.00% for $C_{max}$ and $AUC_{0-72}$.<br>The test product (Fed) will be concluded bioequivalent to the Reference product (Fed) if the limits fall within acceptance range (80.00%-125.00%) of the 90% confidence intervals for the difference of means of log-transformed (Cmax and AUC0-72) with respect to Topiramate. | | |
| Ethical Issues | The study will commence only after a written approval is obtained from the Ethics Committee (EC). The study will be conducted as per New Drugs and Clinical Trials Rules 2019 G.S.R 227(E) dated: 19 Mar. 2019; Ethical Guidelines for Biomedical Research on Human Participants, Good Clinical Laboratory Practice (GCLP), ICMR (Indian Council of Medical Research; 2017), Declaration of Helsinki (64th WMA General Assembly, Fortaleza, Brazil, October 2013), ICH E6 R2 (Step 5) 'Guidance on Good Clinical Practice', Guidance for Industry Bioavailability and Bioequivalence Studies for Orally Administered Drag Products - General Considerations - U. S. Department of Health and Human Service Food and Drug Administration, Center for Drug Evaluation and Research (CDER) March 2003; 21 CFR (Code of Federal Regulations) and all other applicable regulatory requirements. | | |

1.0 Pivotal Study—Protocol Summary—Fasting Study

| | |
|---|---|
| Study Title | An open-label, randomized, balanced, single-dose, two-treatment, two-period, two-sequence, two-way cross-over, oral bioavailability study of Topiramate oral suspension 25 mg/mL Manufactured by OWP Pharmaceuticals, Inc, 400 East Diehl Road, Suite 400, Naperville, IL 60563 with TOPAMAX ® (topiramate) tablets, 100 mg manufactured by Janssen Ortho LLC Gurabo, Puerto Rico 00778 and manufactured for Janssen Pharmaceuticals, Inc. |

| | |
|---|---|
| | Titusville, NJ 08560 in healthy, adult, human, male subjects under fasting conditions. |
| Study Objectives | 1. To compare the oral bioavailability of Topiramate oral suspension 25 mg/mL Manufactured by OWP Pharmaceuticals, Inc, 400 East Diehl Road, Suite 400, Naperville, IL 60563 with TOPAMAX ® (topiramate) tablets 100 mg manufactured by Janssen Ortho LLC Gurabo, Puerto Rico 00778 and manufactured for Janssen Pharmaceuticals, Inc. Titusville, NJ 08560 in healthy, adult, human, male subjects under fasting conditions.<br>2. To evaluate subject safety and tolerability of investigational products. |
| Study Design | An open-label, randomized, balanced, single-dose, two-treatment, two-period, two-sequence, cross-over, oral bioequivalence study in 36 healthy, adult, human, male subjects under fasting conditions. |
| Number of Subjects | Thirty-six (36) healthy, adult, human, male subjects will be enrolled into the study.<br>Two additional subjects will be enrolled to compensate any withdrawn/dropout prior to the dosing of Period-I. If any subject withdraws/drops out due to any reason prior to the dosing in Period-I, he will be replaced with the additional enrolled subjects to ensure the dosing of 36 subjects as per in-house SOP. |
| Investigational Drug Products | Test (T) — Topiramate oral suspension 25 mg/mL Manufactured by: OWP Pharmaceuticals, Inc, 400 East Diehl Road, Suite 400, Naperville, IL 60563<br>Reference (R) — TOPAMAX ® (topiramate) tablets, 100 mg Manufactured by: Janssen Ortho, LLC Gurabo, Puerto Rico 00778 Manufactured for: Janssen Pharmaceuticals, Inc. Titusville, NJ 08560 |
| Washout Period | At least 21 days, between each drug administration. |
| Duration of the period | The minimum duration of this study will be at least 26 days (including a gap of washout period of 21 days between each period of the study). |
| Drug Administration | Subjects should comply at least 10.00 hours overnight fasting prior to drug administration and no food will be allowed at least 4.00 hours post dose in each period.<br>As per the randomization schedule subject will receive Test or Reference product in each period. Subjects will receive Test (T) treatment once and Reference (R) treatment once<br>The clock time when each dose is administered will be recorded on the Case Report Forms.<br>Reference Product Administration:<br><br>One tablet of reference product [TOPAMAX ® (topiramate) tablets, 100 mg] will be administrated to the subject with 240 ± 02 mL of drinking water at room temperature in sitting posture, under fasting conditions.<br>Subjects will be instructed do not chew, crush, or break the tablet and swallow whole.<br>The clinical staff will ensure that the study participant has swallowed the medication by performing mouth check using torchlight and Spatula/tongue depressor.<br>Test product Administration:<br><br>4 mL of test product (Topiramate oral suspension 25 mg/mL) will be slowly administered orally, directly into the corner of the mouth until the liquid medicine in the syringe is completed, to the subjects using a disposable graded syringe at room temperature in sitting posture, under fasted conditions.<br>After subjects swallow oral suspension, the drug-dispensing container (syringe) will be rinsed with an adequate amount of water until it is free of medicine and allowed to swallow the rinse. The remaining amount of water from 240 ± 02 mL will be administered at room temperature in sitting posture, under fasting condition.<br>Subjects will be instructed do not spit the suspension and swallow whole. |
| Admission and Stay | Study participants will be housed in the Clinical Pharmacology Unit (CPU) from at least 11.00 hours before drug administration to 48.00 hours after drug administration. |
| | Sample Management |
| Sampling Time Points | In each period, total 22 (1 × 4 mL) blood samples will be collected as per the following schedule:<br>Pre dose (0.00 hour) sample will be collected within 01 hour prior to drug administration and the post dose samples will be collected at 0.25, 0.50, 0.75, 1.00, 1.25, 1.50, 1.75, 2.00, 2.50, 3.00, 3.50, |

| | In-house | Ambulatory | Total |
|---|---|---|---|
| 4.00, 6.00, 8.00, 10.00, 12.00, 16.00, 24.00, 36.00, 48.00 and 72.00 hours into 4 ml $K_2$EDTA vacutainers | | | |
| | 21 | 01 | 22 |

| | | | |
|---|---|---|---|
| Blood Loss | Screening | | Up to 12 mL |
| | Study | | 176 mL |
| | Discarding the Saline mixed blood | | Up to 17 mL |
| | Post Study | | Up to 12 mL |
| | Total | | Approximately 217 mL |
| Anticoagulant | $K_2$EDTA | | |
| Centrifugation Details | 3800 RPM for 10 minutes at 4° C. ± 2° C. | | |
| Sample Storage Conditions | samples will be stored at −70° C. ± 15° C. until drawn for bioanalysis. | | |
| No. of Aliquots | Two | | |
| Analytical Methods | The plasma concentrations of Topiramate will be quantified in plasma using validated analytical method. | | |
| Pharmacokinetic Parameters | Primary Parameters: $C_{max}$, $AUC_{0-t}$, and $AUC_{0-inf}$. Secondary Parameters: $T_{max}$, $K_{el}$ and $t_{1/2}$. | | |
| Bioequivalence Criteria | Based on the Analysis, Bioequivalence is declared if the Test products (T) and Reference (R) ratios of the geometric least squares means for ln-transformed pharmacokinetic parameters $C_{max}$, $AUC_{0-t}$ and $AUC_{0-inf}$ and their 90% confidence intervals are within 80.00%-125.00% for Topiramate. | | |
| Ethical Issues | The study will commence only after a written approval is obtained from the Ethics Committee (EC). The study will be conducted as per New Drugs and Clinical Trials Rules 2019 G.S.R 227(E) dated: 19 Mar. 2019; Ethical Guidelines for Biomedical Research on Human Participants, Good Clinical Laboratory Practice (GCLP), ICMR (Indian Council of Medical Research; 2017), Declaration of Helsinki (64th WMA General Assembly, Fortaleza, Brazil, October 2013), ICH E6 R2 (Step 5) 'Guidance on Good Clinical Practice', Guidance for Industry Bioavailability and Bioequivalence Studies for Orally Administered Drug Products - General Considerations - U. S. Department of Health and Human Service Food and Drug Administration, Center for Drug Evaluation and Research (CDER) March 2003, 21 CFR (Code of Federal Regulations) and all other applicable regulatory requirements. | | |

Timetable of Events (Example)

The following is a representative time schedule for one subject assuming that the study medication will be administered at 08:00. A wash out period of 07 days will be maintained between each drug administration. Timings for other subjects will be uniformly staggered:

| DAY | TIME RELATIVE TO DOSING (HOURS) | APPROXIMATE TIME | EVENTS |
|---|---|---|---|
| 1 | −24.00 to −11.00 | 08:00 to 21:00 | Compliance Assessment, Check-In and Dinner. |
| 1 | −10.00 to −9.00 | 22:00 to 23:00 | Bedtime |
| 2 | −2.50 | 05:30 | Wakeup call |
| 2 | −2.00 to 0.00 | 06:00 to 08:00 | Pre dose Vitals, Well-being and Cannulation |
| 2 | −1.00 | 07:00 | Water restriction begins |
| 2 | −1.00 to 0.00 | 07:00 to 08:00 | Pre-dose blood sample collection |
| 2 | −0.50 | 07:30 | High fat and high calorie breakfast (Only for fed condition) |
| 2 | 0.00 | 08:00 | Dosing & Posture restriction begins. |
| 2 | 0.25 | 08:15 | Blood sample collection |
| 2 | 0.50 | 08:30 | Blood sample collection |
| 2 | 0.75 | 08:45 | Blood sample collection |
| 2 | 1.00 | 09:00 | Blood sample collection, Vitals, Well-being & Water restriction ends. |
| 2 | 1.25 | 09:15 | Blood sample collection |
| 2 | 1.50 | 09:30 | Blood sample collection |
| 2 | 1.75 | 09:45 | Blood sample collection |
| 2 | 2.00 | 10:00 | Blood sample collection |
| 2 | 2.50 | 10:30 | Blood sample collection |
| 2 | 3.00 | 11:00 | Blood sample collection, Orthostatic vitals & Well-being. |
| 2 | 3.50 | 11:30 | Blood sample collection |
| 2 | 4.00 | 12:00 | Blood sample collection and Lunch |
| 2 | 5.00 | 13:00 | Blood sample collection |
| 2 | 6.00 | 14:00 | Blood sample collection, Orthostatic vitals & Well-being |
| 2 | 7.00 | 15:00 | Blood sample collection |
| 2 | 8.00 | 16:00 | Blood sample collection & Posture restriction ends. |
| 2 | 09.00 | 17:00 | Snacks |
| 2 | 10.00 | 18:00 | Blood sample collection, Vitals & Well-being |
| 2 | 12.00 | 20:00 | Blood sample collection |

-continued

| DAY | TIME RELATIVE TO DOSING (HOURS) | APPROXIMATE TIME | EVENTS |
|---|---|---|---|
| 2 | 13:00 | 21:00 | Dinner |
| 3 | 16.00 | 00:00 | Blood sample collection |
| 3 | 24.00 | 08:00 | Blood sample collection, Vitals & Well-being |
| 3 | 25.00 | 09:00 | Break fast |
| 3 | 28.00 | 12:00 | Vitals & Well-being |
| 3 | 29.00 | 13:00 | Lunch |
| 3 | 33.00 | 17:00 | Snacks |
| 3 | 36.00 | 20:00 | Vitals & Well-being |
| 3 | 37.00 | 21:00 | Dinner |
| 4 | 48.00 | 08:00 | Vitals, Well-being, Check out and Post study assessment. |

Note:
Actual time may change according to the dose administration time.

What is claimed is:

1. A method for treating at least one of a neurological disorder and a mental disorder in a subject, wherein the at least one of a neurological disorder and a mental disorder comprises at least one of (a)-(c):
   (a) epilepsy—adjunctive therapy in a subject aged 2 years or older:
   partial-onset seizures,
   primary generalized tonic-clonic seizures,
   generalized seizures of Lennox-Gastaut syndrome,
   (b) epilepsy—monotherapy in a subject aged 16 years and older: Conversion to monotherapy in a subject with partial-onset seizures who are receiving treatment with carbamazepine, phenytoin, phenobarbital, primidone, or valproate as the single antiepileptic drug (AED), or
   (c) bipolar disorder: maintenance treatment of bipolar I disorder to delay the time to occurrence of mood episodes in a subject treated for acute mood episodes with standard therapy;
   the method comprising administering to a subject suffering from the disorder, 0.1 to 25.0 mL of an oral liquid suspension comprising:
   2,3:4,5-Di-O-isopropylidene-β-fructopyranose sulfamate (topiramate), present in 25±5 mg/mL;
   water;
   glycerin;
   propylene glycol;
   polyethylene glycol;
   methylparaben;
   sodium benzoate;
   sorbitol;
   saccharin;
   sucralose;
   xanthan gum;
   carboxymethyl cellulose (CMC);
   sodium phosphate;
   microcrystalline cellulose; and
   colloidal silicon dioxide.

2. The method of claim 1, wherein the topiramate present in the oral liquid suspension has the following particle size distribution (PSD):
   $D_{90}$ of not more than 200 microns,
   $D_{50}$ of not more than 100 microns, and
   $D_{10}$ of not more than 30 microns.

3. The method of claim 1, wherein the topiramate present in the oral liquid suspension has the following particle size distribution (PSD):
   $D_{90}$ of not more than 139 microns,
   $D_{50}$ of not more than 64.8 microns, and
   $D_{10}$ of not more than 24.65 microns.

4. The method of claim 1, wherein the oral liquid suspension has a viscosity at 25° C. of 300-400 millipoises.

5. The method of claim 1, wherein the oral liquid suspension has a viscosity at 25° C. of 341.7±10 millipoises.

6. The method of claim 1, wherein the oral liquid suspension has a pH of 7.5-7.9.

7. The method of claim 1, wherein the oral liquid suspension has a pH of 7.7±0.1.

8. The method of claim 1, wherein the oral liquid suspension has a specific gravity of not more than 1.1049.

9. The method of claim 1, wherein the oral liquid suspension has a specific gravity of not more than 1.2.

10. The method of claim 1, wherein the oral liquid suspension further comprises a flavoring agent.

11. The method of claim 1, wherein the oral liquid suspension further comprises cherry flavor as a flavoring agent.

12. The method of claim 1, wherein the oral liquid suspension has further comprises a coloring agent.

13. The method of claim 1, wherein the oral liquid suspension further comprises FD&C red #40 and FD&C yellow #6 as a coloring agent.

14. The method of claim 1, wherein the oral liquid suspension comprises:

| Amount (% w/v) | Component |
|---|---|
| 2.5 ± 0.25 | topiramate |
| 0.10 ± 0.01 | methylparaben |
| 0.03 ± 0.003 | sodium benzoate powder |
| 0.08 ± 0.008 | saccharin sodium dihydrate |
| 3.00 ± 0.3 | 70% solution of sorbitol |
| 2.25 ± 0.3 | propylene glycol |
| 5 ± 0.5 | glycerin (99% natural) |
| 1.26 ± 0.15 | (-microcrystalline cellulose and colloidal silicon dioxide-) |
| 0.18 ± 0.02 | sodium carboxymethyl cellulose (medium viscosity, 2% aqueous solution at 25° C. 400-800 cPs) |
| 0.18 ± 0.02 | xanthan gum NF |
| 0.20 ± 0.02 | cherry flavor, natural & artificial |
| 0.002 ± 0.0002 | FD&C Red #40 |
| 0.0002 ± 0.00002 | FD&C Yellow #6 |
| 79.67 ± 8.0 | purified water |
| 5 ± 0.5 | polyethylene glycol 400 |
| 0.25 ± 0.03 | sodium phosphate dibasic (dried) |
| 0.5 ± 0.05 | sucralose |
| TOTAL | |
| 100.2022. | |

15. The method of claim 1, wherein the oral liquid suspension has a volume of 0.2 mL, 0.5 inL, 2.5 mL, 10 mL, 15 mL, or 20 mL.

16. The method of claim 1, wherein the oral liquid suspension, while packaged in a container, is essentially free from microbial growth for at least 24 months under ambient conditions.

17. The method of claim 1, wherein the oral liquid suspension, while packaged in a container, is essentially free from *Escherichia coli* (*E. coli*) for at least 24 months under ambient conditions.

18. The method of claim 1, wherein the oral liquid suspension, while packaged in a container, is essentially free from *Burkholderia cepacia* complex (BCC) for at least 24 months under ambient conditions.

19. The method of claim 1, wherein the oral liquid suspension is an immediate release dosage form.

20. The ethod of claim 1, wherein the oral liquid suspension is an immediate release dosage form that exhibits in-vitro dissolution rate more than 88% of drug release within 30 minutes, when said dosage form is placed in a dissolution vessel filled with 900 ml of 0.1N HCL, pH 1.2 maintained at 37±0.5° C. and stirred at a paddle speed of 50 rpm using a USP Type II (paddle) apparatus.

21. The method of claim 1, wherein the oral liquid suspension is administered, such that
2.5±0.25 mg topiramate in 0.1 mL of the oral liquid suspension, or
5±0.5 mg topiramate in 0.2 mL of the oral liquid suspension, or
10±1.0 mg topiramate in 0.4 mL of the oral liquid suspension, or
12.5±1.25 mg topiramate in 0.5 mL of the oral liquid suspension, or
15±1.5 mg topiramate in 0.6 mL of the oral liquid suspension, or
20±2.0 mg topiramate in 0.8 mL of the oral liquid suspension, or
25±2.5 mg topiramate in 1.0 mL of the oral liquid suspension, or
50±5.0 mg topiramate in 2.0 mL of the oral liquid suspension, or
62.5±6.25 mg topiramate in 2.5 mL of the oral liquid suspension, or
75±7.5 mg topiramate in 3.0 ML of the oral liquid suspension, or
100±10.0 mg topiramate in 4.0 mL of the oral liquid suspension, or
125±12.5 mg topiramate in 5.0 mL of the oral liquid suspension, or
150±15.0 mg topiramate in 6.0 mL of the oral liquid suspension, or
175±17.5 mg topiramate in 7.0 mL of the oral liquid suspension, or
200±20.0 mg topiramate in 8.0 mL of the oral liquid suspension, or
250±25.0 mg topiramate in 10.0 mL of the oral liquid suspension is delivered to the subject.

22. The method of claim 1, wherein upon administration under fasted conditions of a healthy adult subject with epilepsy taking no other medications, the oral liquid suspension exhibits a single-dose administration pharmacokinetic (PK) profile including:
AUC, 0→24 (micrograms per ml) of 98-105;
Cmax (micrograms per ml) steady state of 1.5;
$T_{max}^{(h)}$ of 2-3;
$t_{1/2}^{(h)}$ of 19-25 (single dose); and
$t_{1/2}^{(h)}$ of 19-25 (multiple dose).

23. The method of claim 1, wherein relative to oral tablets or chewable dispersible tablets containing an equivalent amount of topiramate, administration of the oral liquid suspension results in a lower incidence, severity, and/or duration of adverse reactions including at least one of dizziness, headache, diplopia, ataxia, nausea, blurred vision, somnolence, rhinitis, pharyngitis, rash, vomiting, infection, fever, accidental injury, diarrhea, abdominal pain, tremor, insomnia, somnolence, backpain, fatigue, abdominal pain, and xerostomia.

* * * * *